US012257246B2

(12) United States Patent
Pilgrim et al.

(10) Patent No.: US 12,257,246 B2
(45) Date of Patent: Mar. 25, 2025

(54) COMPOSITION OF 2,4,6-TRIFLUORO-N-[6-(1-METHYL-PIPERIDIN-4-CARBONYL)-PYRIDIN-2-YL[-BENZAMIDE

(71) Applicant: CoLucid Pharmaceuticals, Inc., Indianapolis, IN (US)

(72) Inventors: Alison Pilgrim, La Jolla, CA (US); James F. White, Carlisle, MA (US); Nadia M. J. Rupniak, Cary, NC (US)

(73) Assignee: COLUCID PHARMACEUTICALS, INC., Indianapolis, IN (US)

( * ) Notice: Subject to any disclaimer, the term of this patent is extended or adjusted under 35 U.S.C. 154(b) by 96 days.

(21) Appl. No.: 17/474,203

(22) Filed: Sep. 14, 2021

(65) Prior Publication Data

US 2021/0401822 A1   Dec. 30, 2021

Related U.S. Application Data

(63) Continuation of application No. 12/753,489, filed on Apr. 2, 2010, now abandoned.

(60) Provisional application No. 61/166,097, filed on Apr. 2, 2009.

(51) Int. Cl.
*A61K 31/4545* (2006.01)

(52) U.S. Cl.
CPC .............................. *A61K 31/4545* (2013.01)

(58) Field of Classification Search
CPC ............ A61K 31/4545; A61K 2121/00; A61K 9/0019; A61K 9/0031; A61K 9/0053
See application file for complete search history.

(56) References Cited

U.S. PATENT DOCUMENTS

| | | | |
|---|---|---|---|
| 5,011,472 A | 4/1991 | Aebischer et al. |
| 5,023,252 A | 6/1991 | Hseih et al. |
| 5,385,912 A | 1/1995 | Neuenschwander et al. |
| 5,521,196 A | 5/1996 | Audia et al. |
| 5,521,197 A | 5/1996 | Audia et al. |
| 5,698,571 A | 12/1997 | Audia et al. |
| 5,708,008 A | 1/1998 | Audia et al. |
| 5,708,187 A | 1/1998 | Flaugh et al. |
| 5,721,252 A | 2/1998 | Audia et al. |
| 5,814,653 A | 9/1998 | Flaugh et al. |
| 5,817,671 A | 10/1998 | Filla et al. |
| 6,528,529 B1 | 3/2003 | Brann et al. |
| 6,650,463 B2 | 11/2003 | Obikawa et al. |
| 6,777,428 B1 | 8/2004 | Krushinski, Jr. et al. |
| 7,291,632 B2 | 11/2007 | Blanco-Pillado et al. |
| 7,423,050 B2 | 9/2008 | Cohen et al. |
| 7,608,629 B2 | 10/2009 | Blanco-Pillado et al. |
| 8,044,207 B2 | 10/2011 | Mancuso et al. |
| 8,697,876 B2 | 4/2014 | Carniaux et al. |
| 8,748,459 B2 | 6/2014 | Cohen et al. |
| 2002/0175891 A1 | 11/2002 | Obikawa et al. |
| 2003/0144285 A1 | 7/2003 | Brann |
| 2003/0175445 A1 | 9/2003 | Kirsch et al. |
| 2005/0009871 A1 | 1/2005 | Ramesh et al. |
| 2005/0080112 A1 | 4/2005 | Madsen et al. |
| 2006/0211734 A1 | 9/2006 | Bianco-Pillado et al. |
| 2007/0129354 A1 | 6/2007 | Aston et al. |
| 2007/0219187 A1 | 9/2007 | Bessis et al. |
| 2007/0299110 A1 | 12/2007 | Gagliardi et al. |
| 2008/0300407 A1 | 12/2008 | Cohen et al. |

FOREIGN PATENT DOCUMENTS

| | | |
|---|---|---|
| EP | 1492786 B1 | 3/2003 |
| EP | 10759491.3 | 8/2020 |
| JP | 03255426 A | 11/1991 |
| KR | 2006-0067738 A | 6/2006 |
| WO | 9314201 A2 | 7/1993 |
| WO | 9629075 A1 | 9/1996 |
| WO | 9713512 A1 | 4/1997 |
| WO | 9808502 A1 | 3/1998 |
| WO | 9815545 A1 | 4/1998 |
| WO | 9820875 A1 | 5/1998 |
| WO | 9846570 A1 | 10/1998 |
| WO | 9855115 A1 | 12/1998 |
| WO | 9925348 A1 | 5/1999 |
| WO | 0000487 A1 | 1/2000 |
| WO | 0000490 A2 | 1/2000 |
| WO | 0034266 A1 | 6/2000 |
| WO | 0047559 A2 | 8/2000 |
| WO | 0050426 A2 | 8/2000 |
| WO | 200105763 A2 | 1/2001 |
| WO | 200206196 A1 | 1/2002 |
| WO | 2003000245 A1 | 1/2003 |
| WO | 03084949 A1 | 10/2003 |
| WO | 04047739 A2 | 6/2004 |
| WO | 2004089874 A1 | 10/2004 |
| WO | 2004089874 A2 | 10/2004 |
| WO | 2004099127 A1 | 11/2004 |
| WO | 2005-007621 A2 | 1/2005 |
| WO | 2005044797 A1 | 5/2005 |
| WO | 2006048771 A1 | 5/2006 |

(Continued)

OTHER PUBLICATIONS

Limmroth V, Diener HC. New anti-migraine drugs: present and beyond the millennium. Int J Clin Pract. Nov.-Dec. 1998; 52(8):566-70.

Lipton RB, Cutrer FM, Goadsby PJ, Ferrari MD, Dodick DW, McCrory D, Liberman JN, Williams P. How treatment priorities influence triptan preferences in clinical practice: perspectives of migraine sufferers, neurologists, and primary care physicians. Curr Med Res Opin. Mar. 2005; 21(3):413-24.

Cutrer FM, Goadsby PJ, Ferrari MD, Lipton RB, Dodick DW, McCrory D, Williams P. Priorities for triptan treatment attributes and the implications for selecting an oral triptan for acute migraine: a study of US primary care physicians (the TRIPSTAR Project). Clin Ther. Sep. 2004; 26(9):1533-45.

(Continued)

*Primary Examiner* — Jeffrey S Lundgren
*Assistant Examiner* — Michael J Schmitt
(74) *Attorney, Agent, or Firm* — Dan L. Wood

(57) ABSTRACT

The present invention relates to discloses a pharmaceutical composition of 2,4,6-trifluoro-N-[6-(1-methyl-piperidin-4-ylcarbonyl)-pyridin-2-yl]-benzamide and a pharmaceutically acceptable carrier.

5 Claims, 17 Drawing Sheets

(56) References Cited

FOREIGN PATENT DOCUMENTS

| WO | 2006058905 A1 | 6/2006 |
| WO | 2006081127 A2 | 8/2006 |
| WO | 2006108487 A1 | 10/2006 |
| WO | 08114971 A1 | 9/2008 |
| WO | 2010115125 A2 | 10/2010 |
| WO | 11123654 A1 | 10/2011 |
| WO | 2018106657 | 6/2018 |
| WO | 2019/050759 A1 | 3/2019 |
| WO | 2020/051137 A1 | 3/2020 |
| WO | 2021/007155 A1 | 1/2021 |

OTHER PUBLICATIONS

Lipton RB, Hamelsky SW, Dayno JM. What do patients with migraine want from acute migraine treatment? Headache 2002; 42(suppl. 1):3-9.

Kuca B, Silberstein SD, Wietecha L, Berg PH, Dozier G, Lipton RB; COL MIG-301 Study Group. Lasmiditan is an effective acute treatment for migraine: A phase 3 randomized study. Neurology. Dec. 11, 2018; 91(24): e2222-e2232.

Goadsby PJ, Wietecha LA, Dennehy EB, Kuca B, Case MG, Aurora SK, Gaul C. Phase 3 randomized, placebo-controlled, double-blind study of lasmiditan for acute treatment of migraine. Brain. Jul. 1, 2019;142(7):1894-1904.

Shapiro RE, Hochstetler HM, Dennehy EB, Khanna R, Doty EG, Berg PH, Starling AJ. Lasmiditan for acute treatment of migraine in patients with cardiovascular risk factors: post-hoc analysis of pooled results from 2 randomized, double-blind, placebo-controlled, phase 3 trials. J Headache Pain. Aug. 29, 2019;20(1):90.

Ashina M, Vasudeva R, Jin L, Lombard L, Gray E, Doty EG, Yunes-Medina L, Kinchen KS, Tassorelli C. Onset of Efficacy Following Oral Treatment With Lasmiditan for the Acute Treatment of Migraine: Integrated Results From 2 Randomized Double-Blind Placebo-Controlled Phase 3 Clinical Studies. Headache. Nov. 2019; 59(10):1788-1801.

Doty EG, Krege JH, Jin L, Raskin J, Halker Singh RB, Kalidas K. Sustained responses to lasmiditan: Results from post-hoc analyses of two Phase 3 randomized clinical trials for acute treatment of migraine. Cephalalgia. Oct. 2019; 39(12):1569-1576.

Knievel K, Buchanan AS, Lombard L, Baygani S, Raskin J, Krege JH, Loo LS, Komori M, Tobin J. Lasmiditan for the acute treatment of migraine: Subgroup analyses by prior response to triptans. Cephalalgia. Jan. 2020; 40(1):19-27.

Loo LS, Ailani J, Schim J, Baygani S, Hundemer HP, Port M, Krege JH. Efficacy and safety of lasmiditan in patients using concomitant migraine preventive medications: findings from Samurai and Spartan, two randomized phase 3 trials. J Headache Pain. Jul. 24, 2019;20(1):84.

Clemow, DB, Johnson, KW, Hochstetler, HM, Ossipov MH, Hake AM, Blumenfeld AM. Lasmiditan mechanism of action—review of a selective 5-HT1F agonist. J Headache Pain 21, 71 (2020).

Vargas B, Magis D, Doty E, Ruff D, Vasudeva R, Krege JH, Hake A. Assessment to identify predictors of 2-hour pain freedom among patients enrolled in two phase 3 studies of lasmiditan for acute treatment of migraine. International Headache Society—19th International Headache Congress 2019.

Adham et al., "Cloning of another human serotonin receptor (5-HT1F): A Fifth 5-HT1 receptor subtype coupled to the inhibition of adenylate cyclase", Proc. Natl. Acad. Sci. U.S.A., 90:408-412 (1993).

"A Placebo-Controlled Adaptive Treatment Assignment Study of Intravenous COL-144 in the Acute Treatment of Migraine—Study 2 of 2 for search of: Colucid", Clinical Trials, Oct. 4, 2006 (4 pages).

"Dose-ranging Study of Oral COL-144 in Acute Migraine Treatment—Study 1 of 2 for search of: Colucid", Clinical Trials, Apr. 16, 2009 (5 pages).

Japanese Abstract for JP 03255426 (Nov. 14, 1991), Toshiba Corp., Japan.

King, F.D., "Bioisosteres, Conformational Restriction, and Pro-drugs—Case History: An Example of a Conformational Restriction Approach", in *Medicinal Chemistry: Principles and Practice*, Royal Society of Chemistry, Cambridge, England, Ch. 14, pp. 206-209 (1994).

Phebus et al., "Characterization of LY344864 as a Pharmacological Tool to Study 5-HT1F Receptors: Binding Affinities, Brain Penetration and Activity in the Neurogenic Dural Inflammational Model of Migraine", *Life Sciences*, 61(21), 2117-2126 (1997) (Abstract Only).

Radl et al., "Synthesis and Antinociceptive Activity of Some 3-Chlorophenyl- and 6-Chloro-2 Pyridinyl Derivatives", *Coll. Czech. Chem. Comm.*, 64(2):377-388 (1999) (Abstract Only).

Pringsheim et al. "Prophylaxis of migraine headache", CMAJ, 2010, 182(7), pp. E269-E276.

Berge et al. "Pharmaceutical Salts." J. Pham. Sci 66.1 (1977):1-19.

Ferrari et al. "Oral Triptans (Serotonin 5-HT1B/1D Agonists) in Acute Migraine Treatment: A Meta-Analysis of 53 Trials." Lancet. 358(2001):1668-1675.

Goadsby et al. "Migraine—Current Understanding and Treatment," N. Engl J. Med. 346.4(2002):257-270.

Goldstein et al. "Selective Seratonin 1F (5-HT1F) Receptor Agonist LY334370 for Acute Migraine: A Randomised Controlled Trial," Lancet. 358.9289(2001):1230-1234.

Graham et al. "Mechanism of Migraine Headache and Action of Ergotamine Tartrate." Arc. Neurol. Psychiatry, 39.4(1938):737-763.

Gros et al. "Aggregative Activation in Heterocyclic Chemistry. Part 5, Lithiation of Pyridine and Quinoline with the Complex Base BuLi-Me2N(CH2)2OLi(BuLi-LiDMAE)." J. Chem Soc., Perkin Trans. 1 24(1997):3597-3600.

Hall et al. "A Group Sequential Adaptive Treatment Assignment Design for Proof of Concept and Dose Selection in Headache Trials." Contemp. Clin. Trials 26.3(2005):349-364.

Headache Classification Subcommittee of the International Headache Society. "The International Classification of Headache Disorders: Second Edition." Cephalalgia. 24.S11(2004):1-160.

Herrick-Davis et al. "Detection and Characterization of the Serotonin 5-HT1D Receptor in Rat and Human Brain." J. Neurochem. 50.5(1988):1624-1631.

Ho et al. "Efficacy and Tolerability of MK-0974 (telcagepant), a New Oral Antagonist of Calcitonin Gene-Related Peptide Receptor, Compared with Zolmitriptan for Acute Migraine: A Randomised, Placebo- Controlled, Parallel-Treatment Trial." Lancet. 372. 9656(2008):2115-2123.

Humphrey et al. "Serotonin and Migraine." Ann. N.Y. Acad. Sci. 600(1990):587-598.

International Headache Society Clinical Trials Subcommittee. "Guidelines for Controlled Trials of Drugs in Migraine: Second Edition." Cephalalgia. 20.9(2000):765-786.

Maassenvandenbrink et al. "Coronary Side-Effect Potential of Current and Prospective Antimigraine Drugs." Circulation. 98. 1(1998):25-30.

Moskowitz. "Interpreting Vessel Diameter Changes in Vascular Headaches." Cephalalgia. 12.1(1992):5-7.

Moskowitz. "Neurogenic Inflammation in the Pathophysiology and Treatment of Migraine." Neurol. 43.S3(1993):S6-S20.

Nelson et al. COL-144: Preclinical Profile of a Selective 5-HT1R Receptor Agonist for Migraine. Cephalalgia. 29(2009):122-123. (Abstract # PC. 12).

Olesen et al. "Calcitonin Gene-Related Peptide Receptor Antagonist BIBN 4096 BS for the Acute Treatment of Migraine." N. Engl. J. Med. 350.11(2004):11404-1110.

Schoonman et al. "Migraine Headache is not Associated with Cerebral of Meningeal Vasodilation—a 3 T Magnetic Resonance Angiography Study." Brain. 131.Pt8(2008):2192-2200.

Stovner et al. "The Global Burden of Headache: A Documentation of Headache Prevalence and Disability Worldwide." Cephalalgia. 27.3(2007)193-210.

Visser et al. "Chest Symptoms After Sumatriptan: A Two-Year Clinical Practice Review in 735 Consecutive Migraine Patients." Cephalalgia. 16.8(1996):554-559.

(56) References Cited

OTHER PUBLICATIONS

Weinshank et al. "Human Serotonin 1D Receptor is Encoded by a Subfamily of Two Distinct Genes: 5-HT1Da and 5-HT1DB." PNAS. 89.8(1992):3630-3634.
Welch et al. "Tolerability of Sumatriptan: Clinical Trails and Post-Marketing Experience." Cephalalgia. 20.8(2000):687-695.
"Metallation." Introduction to Organic Chemistry. Streitwieser et al., eds. Upper Saddle River, NJ: Prentice Hall. (1992):1011-1012.
Cephalalgia 2009, 29, 122-123 Abstracts of the European Headache and Migraine Trust International Congress 2008, Sep. 4-7, 2008, abstract PC.12 of Nelson entitled "COL-144: Preclinical profile of a selective 5-HT1F receptor agonist for migraine" (D3a) and related poster (D3b).
Cephalalgia 2009, 29, 122-123 Abstracts of the European Headache and Migraine Trust International Congress 2008, Sep. 4-7, 2008, abstract PC.11 of Reuter entitled "COL-144, a selective 5-HT1F agonist, for the treatment of migraine attacks" (D4a) and related poster (D4b).
Press release of CoLucid Pharmaceuticals Inc. entitled "Phase II Results of COL-144 Presented at European Headache and Migraine Trust International Congress 2008", Sep. 6, 2008.
Drug Data Report 2009, 31(10), 964.
Cephalalgia 29 (Suppl. 1) (2009) 24-25 "14$^{th}$ Congress of the International Headache Society Sep. 10-13, 2009, Philadelphia, PA", abstract PO33 of Liefaard entitled "Prediction of therapeutically effective dose of OL-144 based on relationship between plasma concentrations and headache response" (D7a) and related poster (D7b).
Cephalalgia 29 (Suppl. 1) (2009) 24-25 "14$^{th}$ Congress of the International Headache Society Sep. 10-13, 2009, Philadelphia, PA", abstract PO34 of Pilgrim entitled "COL-144, an orally bioavailable selective 5-HT1F receptor agonist for acute migraine therapy" (D8a) and related poster (D8b).
Clinical trial record NCT00883051 as stored in the internet archive of Aug. 9, 2009.
WHO Drug Information, vol. 23, No. 4, 2009, 322-323.
EMEA "Note for guidance on general considerations for clinical trials", Mar. 1998.
Reuter et al., "COL-144: A Selective 5-HT1F Agonist For the Treatment of Migraine Attacks" Cephalalgia, vol. 29, Jan. 2009.
Information about publication date of Reuter et al. (2009) Cephalalgia, 29(1): 101-178.
U.S. National Library of Medicine, "Dose-ranging Study of Oral COL-144 in Acute Migraine Treatment" Apr. 16, 2009.
Lancet Neurol 2012; 11:405-13, Farkkila, M et al., Efficacy and tolerability of Lasmiditan, an oral 5-HT1F receptor agonist, for the acute treatment of migraine: a phase 2 randomised, placebo-controlled, parallel-group, dose-ranging study.
Zhang, D. et al. (Dec. 20, 2004). "Design, synthesis and evaluation of bicyclic benzamides as novel 5-HT1F receptor agonists," *Bioorg Med Chem Lett* 14(24):6011-6016.
Diener et al "The Importance of Placebo in Headache Research." *Cephalalgia*, 28.10 (2008):1003-1011.
WO 2003/084949 Oct. 2003, U.S. Appl. No. 10/509,770, U.S. Pat. No. 7,423,050 Sep. 2008 Cohen.
U.S. Appl. No. 12/220,225, U.S. Pat. No. 8,044,207 Oct. 2011 Mancuso.
U.S. Appl. No. 13/363,895, U.S. Pat. No. 8,748,459 Jun. 2014 Cohen.
WO 2018/106657 Jun. 2018, U.S. Appl. No. 16/467,208, U.S. Pat. No. 11,053,214 Jul. 2021, Allieri.
WO 2019/050759 Mar. 2019, U.S. Appl. No. 16/643,668.
WO 2020/051137 Mar. 2020, U.S. Appl. No. 17/271,950.
WO 2021/007155 Jan. 2021, U.S. Appl. No. 62/871,965.
WO/2022/236004 Nov. 2022, U.S. Appl. No. 18/557,666.

Numbers in bars are N treated at each dose

COMPOSITION OF 2,4,6-TRIFLUORO-N-[6-(1-METHYL-PIPERIDIN-4-CARBONYL)-PYRIDIN-2-YL[-BENZAMIDE

RELATED APPLICATION

This application claims priority under 35 U.S.C. § 119 to U.S. Ser. No. 61/166,097, filed Apr. 2, 2009, the contents of which are incorporated herein.

BACKGROUND OF THE INVENTION

Migraine is a common and highly disabling brain disorder, affecting over 10% of adults globally (Stovner L I et al., Cephalalgia 2007; 27:193-210). The disease is typically characterized by attacks of 1-3 days of severe headache, associated with nausea, vomiting, photo- and phonophobia (migraine without aura), and, in one third of patients, neurological aura symptoms (migraine with aura) (Goadsby P J et al., N Engl J Med 2002; 346: 257-270). The pathogenesis of migraine is incompletely understood. Traditionally, vasodilatation was considered pivotal in causing the headache in migraine (Wolff s Headache and Other Head Pain. Ed Silberstein et al., Oxford University Press, 2001). Triptans, selective 5-$HT_{1B/1D}$ receptor agonists with established antimigraine efficacy (Ferrari M D et al., Lancet 2001: 358; 1668-1675), were developed based on the assumption that 5-$HT_{1B}$ receptor-mediated cranial vasoconstriction is a prerequisite for antimigraine efficacy (Humphrey P P A et al., Ann NY Acad Sci 1990; 600: 587-598). As a consequence, triptans also carry the risk of causing coronary vasoconstriction (MaassenVanDenBrink A et al., Circulation 1998; 98: 25-30) and are contraindicated in patients with cardio- and cerebrovascular disease. In addition, many patients using triptans report chest symptoms, which may mimic angina pectoris, causing anxiety and diagnostic confusion (Welch K M A et al., Cephalalgia 2000; 20: 687-95; Visser W H, et al., Cephalalgia 1996; 16: 554-559). Thus, novel anti-migraine treatments that are devoid of vasoconstrictor activity are warranted.

In recent decades, it has become evident that cranial vasodilation, if it happens at all during a migraine attack (Schoonman G G et al., Brain 2008; 131: 192-200), may only be a secondary phenomenon due to activation of the trigeminovascular system (Goadsby P J et al., N Engl J Med 2002; 346: 257-270). Vasoconstriction may thus not be necessary to treat migraine headaches. Rather, neural inhibition of trigeminal pathways would provide an attractive alternative non-vascular antimigraine mechanism. Indeed, LY334370, a neurally active selective 5-HT1F receptor agonist with no vasoconstrictor activity at clinically relevant concentrations, proved effective in the acute treatment of migraine in an early clinical proof-of-concept study (Goldstein D J et al., Lancet 2001; 358: 1230-4). Unfortunately, the clinical development of LY334370 had to be stopped because of compound-specific safety concerns on long term exposure in animals.

2,4,6-trifluoro-N-[6-(1-methyl-piperidin-4-ylcarbonyl)-pyridin-2-yl]-benzamide (Compound I) is a new selective and highly potent 5-$HT_{1F}$ receptor agonist, with a Ki at human 5-HT1F receptors of 2.21 nM and an affinity which is more than 450-fold higher for 5-$HT_{1F}$ receptors than for other 5-HT1 receptor subtypes (Nelson D L et al., Cephalalgia 2009; 29; 122). U.S. Pat. No. 7,423,050 and U.S. Publication No. 20080300407 describe Compound I, and other selective pyridinoylpiperidine 5-$HT_{1F}$ agonists, which are active in neurally mediated preclinical models of migraine, without causing vasoconstriction (i.e., neutrally active anti-migraine agents (NAANAs)). Experiments in the above-referenced publications demonstrate potent inhibition of c-Fos induction in the trigeminal nucleus caudalis and inhibition of dural plasma protein extravasation following electrical stimulation of the trigeminal ganglion. At concentrations up to 0.1 mM, Compound I did not constrict rabbit saphenous vein, a surrogate assay for human coronary vasoconstrictor liability (Nelson D L et al., Cephalalgia 2009: 29; 122).

SUMMARY OF THE INVENTION

The present invention relates to a pharmaceutical composition of 2,4,6-trifluoro-N-[6-(1-methyl-piperidin-4-yl-carbonyl)-pyridin-2-yl]-benzamide (Compound I):

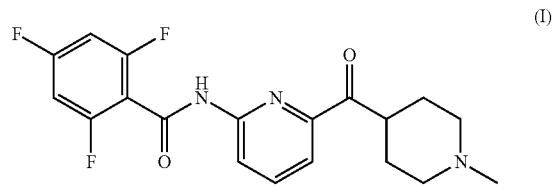 [SMILES: CN1CCC(C(=O)c2cccc(NC(=O)c3c(F)cc(F)cc3F)n2)CC1]

or a pharmaceutically acceptable salt thereof for use in the treatment of migraine.

The present invention relates to a pharmaceutical composition comprising an amount of Compound I or a pharmaceutically acceptable salt thereof and a pharmaceutically acceptable diluent or carrier, wherein for oral or rectal administration said composition comprises 50-400 mg per dose of Compound I or a pharmaceutically acceptable salt thereof and for buccal, sublingual, nasal/intranasal, transdermal, subcutaneous, injectable, intravenous or intramuscular administration said composition comprises up to 200 mg per dose of Compound I or a pharmaceutically acceptable salt thereof, further wherein said composition is administered one, two, or three times daily.

The present invention relates to a pharmaceutical composition, wherein said composition is for oral or rectal administration and the amount of Compound I or pharmaceutically acceptable salt thereof is from 50 mg to 400 mg per dose.

The present invention relates to a pharmaceutical composition, wherein the amount of Compound I is 50 mg per dose. The present invention relates to a pharmaceutical composition, wherein the amount of Compound I is 100 mg per dose. The present invention relates to a pharmaceutical composition, wherein the amount of Compound I is 200 mg per dose. The present invention relates to a pharmaceutical composition, wherein the amount of Compound I is 400 mg per dose.

The present invention relates to a pharmaceutical composition, wherein said composition is for buccal, sublingual, nasal/intranasal, transdermal, subcutaneous, injectable, intravenous, or intramuscular administration and the amount of Compound I or pharmaceutically acceptable salt thereof administered is up to 200 mg per dose.

The present invention relates to a pharmaceutical composition, wherein the amount of Compound I or a pharmaceutically acceptable salt thereof administered is 20 mg to 200 mg per dose. The present invention relates to a pharmaceutical composition, wherein the amount of Compound I or a pharmaceutically acceptable salt thereof administered is from 20 to 60 mg per dose. The present invention relates to a pharmaceutical composition, wherein the amount of Compound I or a pharmaceutically acceptable salt thereof administered is from 20 to 30 mg per dose.

The present invention relates to a pharmaceutical composition, wherein the administration is intravenous and the amount of Compound I or a pharmaceutically acceptable salt thereof administered is up to 200 mg per dose.

The present invention relates to a pharmaceutical composition, wherein the administration of Compound I or a pharmaceutically acceptable salt thereof is intravenous over a period of about 20 minutes.

The present invention relates to a pharmaceutical composition, wherein the composition comprises the hemisuccinate salt of Compound I.

The present invention relates to a pharmaceutical composition, wherein the dose of Compound I or a pharmaceutically acceptable salt thereof is administered one time daily. The present invention relates to a pharmaceutical composition, wherein the dose of Compound I or a pharmaceutically acceptable salt thereof is administered two times daily. The present invention relates to a pharmaceutical composition, wherein the dose of Compound I or a pharmaceutically acceptable salt thereof is administered three times daily.

The present invention relates to a method for the treatment or prevention of migraine in a mammal in need thereof comprising administering to the mammal an effective amount of a pharmaceutical composition, wherein said composition comprises an amount of Compound I or a pharmaceutically acceptable salt thereof and a pharmaceutically acceptable diluent or carrier, further wherein for oral or rectal administration said composition comprises 50-400 mg per dose of Compound I or a pharmaceutically acceptable salt thereof and for buccal, sublingual, nasal/intranasal, transdermal, subcutaneous, injectable, intravenous or intramuscular administration said composition comprises up to 200 mg per dose of Compound I or a pharmaceutically acceptable salt thereof, and wherein said composition is administered one, two, or three times daily. The present invention relates to a method comprising administering an amount of 20 mg of 2,4,6-trifluoro-N-[6-(1-methyl-piperidin-4-ylcarbonyl)-pyridin-2-yl]-benzamide hemisuccinate salt by intravenous administration over 20 minutes one time daily. The present invention relates to a method, wherein said amount of 2,4,6-trifluoro-N-[6-(1-methyl-piperidin-4-ylcarbonyl)-pyridin-2-yl]-benzamide hemisuccinate salt is administered for the prevention of migraine. The present invention relates to a method, wherein the mammal is a human.

BRIEF DESCRIPTION OF THE DRAWINGS

The foregoing and other objects, features, and advantages of the invention will be apparent from the following more particular description of preferred embodiments of the invention, as illustrated in the accompanying drawings. The drawings are not necessarily to scale, emphasis instead being placed upon illustrating the principles of the invention.

FIG. 11A shows dose linearity of solution, AUC∞ (males). FIG. 11B shows dose linearity of tablet, AUC∞ (males and females).

DETAILED DESCRIPTION OF THE INVENTION

Figure 1:
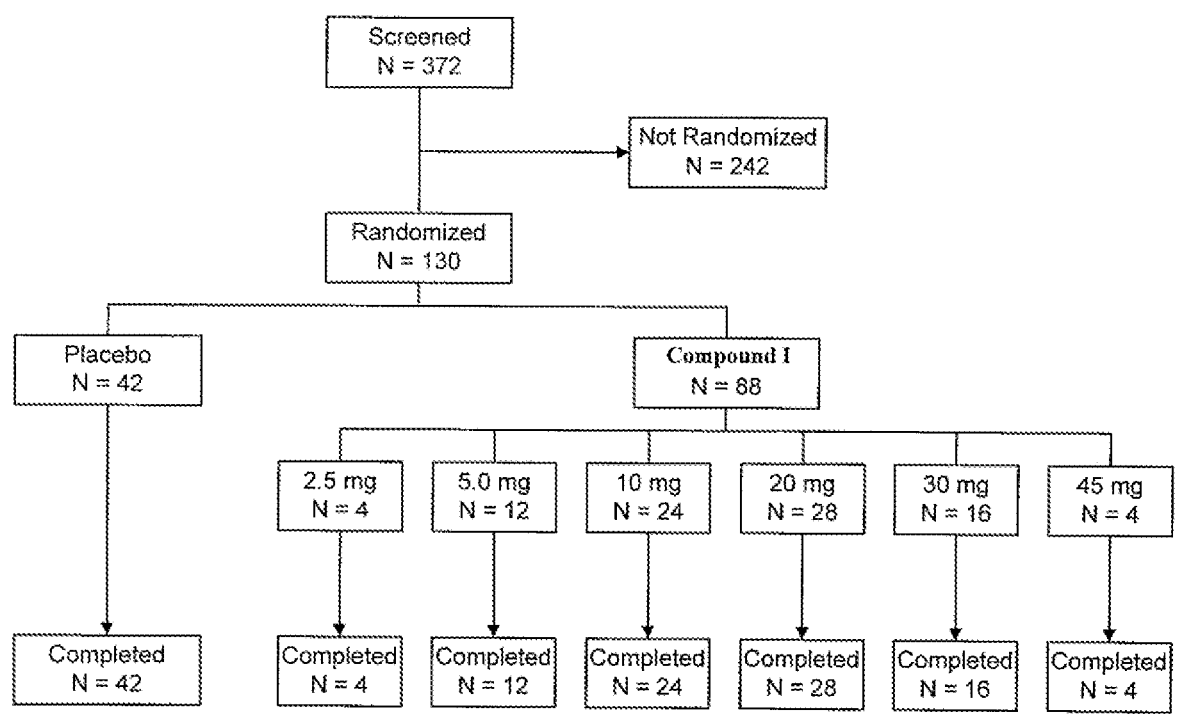
FIG. 1 is a graph that shows the sequence of patient allocation to treatment groups for a study involving the administration of Compound I.

The present invention relates to a pharmaceutical composition comprising 2,4,6-trifluoro-N-[6-(1-methyl-piperidin-4-ylcarbonyl)-pyridin-2-yl]-benzamide (Compound I):

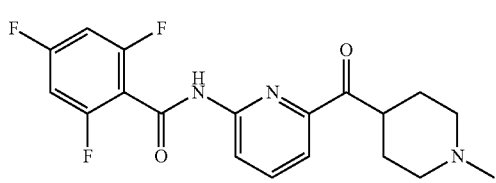

or a pharmaceutically acceptable salt thereof and a pharmaceutically acceptable diluent or carrier. The present invention also relates to a method for the treatment or prevention of migraine in a mammal in need thereof comprising administering to a mammal in need of such treatment or prevention an effective amount of a pharmaceutical composition described herein. The present invention also relates to use of an amount of Compound I or a pharmaceutically acceptable salt thereof, for the preparation of a medicament for the treatment of migraine in a mammal.

Specifically, the present invention relates to a pharmaceutical composition comprising an amount of Compound I or a pharmaceutically acceptable salt thereof and a pharmaceutically acceptable diluent or carrier, wherein for oral or rectal administration said composition comprises 50 to 400 mg per dose of Compound I or a pharmaceutically acceptable salt thereof and for buccal, sublingual, nasal/intranasal, transdermal, subcutaneous, injectable, intravenous or intramuscular administration said composition comprises up to 200 mg per dose of Compound I or a pharmaceutically acceptable salt thereof, further wherein said composition is administered one, two, or three times daily.

The invention relates to a pharmaceutical composition for oral or rectal administration comprising an amount of Compound I or a pharmaceutically acceptable salt thereof, ranging up to 1000 mg per dose administered once, two, or three times daily and a pharmaceutically acceptable diluent or carrier.

In one aspect, the invention relates to a pharmaceutical composition for oral or rectal administration comprising an amount of Compound I or a pharmaceutically acceptable salt, wherein the amount is from 50 mg to 500 mg per dose. In one aspect, the invention relates to a pharmaceutical composition for oral or rectal administration comprising an amount of Compound I or a pharmaceutically acceptable salt, wherein the amount is from 50 mg to 400 mg per dose. In one aspect, the invention relates to a pharmaceutical composition for oral or rectal administration comprising an amount of Compound I or a pharmaceutically acceptable salt, wherein the amount is 50 mg per dose. In one aspect, the invention relates to a pharmaceutical composition for oral or rectal administration comprising an amount of Compound I or a pharmaceutically acceptable salt, wherein the amount is 100 mg per dose. In one aspect, the invention relates to a pharmaceutical composition for oral or rectal administration comprising an amount of Compound I or a pharmaceutically acceptable salt, wherein the amount is 200 mg per dose. In one aspect, the invention relates to a pharmaceutical composition for oral or rectal administration comprising an amount of Compound I or a pharmaceutically acceptable salt, wherein the amount is 400 mg per dose.

In one aspect, the invention relates to a pharmaceutical composition comprising an amount of Compound I or a pharmaceutically acceptable salt, wherein the administration is oral. In one aspect, the invention relates to a pharmaceutical composition comprising an amount of Compound I or a pharmaceutically acceptable salt, wherein the administration is oral administration of a tablet. In one aspect, the table comprises 50 to 400 mg of Compound I or a pharmaceutically acceptable salt thereof. In one aspect, the invention relates to a pharmaceutical composition comprising an amount of Compound I or a pharmaceutically acceptable salt, wherein the administration is oral administration of a solution. In one aspect, the solution comprises 25 to 400 mg of Compound I or a pharmaceutically acceptable salt thereof. In one aspect, the invention relates to a pharmaceutical composition comprising an amount of Compound I or a pharmaceutically acceptable salt, wherein the administration is rectal.

The invention relates to a pharmaceutical composition for buccal, sublingual, nasal/intranasal, transdermal, subcutaneous, injectable, intravenous, or intramuscular administration comprising an amount of Compound I or a pharmaceutically acceptable salt thereof, ranging up to 200 mg per dose administered once, two or three times daily and a pharmaceutically acceptable diluent or carrier.

In one aspect, the invention relates to a pharmaceutical composition for buccal, sublingual, nasal/intranasal, transdermal, subcutaneous, injectable, intravenous, or intramuscular administration comprising an amount of Compound I or a pharmaceutically acceptable salt thereof, wherein the amount is from 20 to 200 mg per dose.

In one aspect, the invention relates to a pharmaceutical composition for buccal, sublingual, nasal/intranasal, transdermal, subcutaneous, injectable, intravenous, or intramuscular administration comprising an amount of Compound I or a pharmaceutically acceptable salt thereof, wherein the amount is from 20 to 100 mg per dose.

In one aspect, the invention relates to a pharmaceutical composition for buccal, sublingual, nasal/intranasal, transdermal, subcutaneous, injectable, intravenous, or intramuscular administration comprising an amount of Compound I or a pharmaceutically acceptable salt thereof, wherein the amount is above 20 mg per dose.

In one aspect, the invention relates to a pharmaceutical composition for buccal, sublingual, nasal/intranasal, transdermal, subcutaneous, injectable, intravenous, or intramuscular administration comprising an amount of Compound I or a pharmaceutically acceptable salt thereof, wherein the amount is from 20 to 60 mg per dose.

In one aspect, the invention relates to a pharmaceutical composition for buccal, sublingual, nasal/intranasal, transdermal, subcutaneous, injectable, intravenous, or intramuscular administration comprising an amount of Compound I or a pharmaceutically acceptable salt thereof, wherein the amount is from 20 to 45 mg per dose.

In one aspect, the invention relates to a pharmaceutical composition for buccal, sublingual, nasal/intranasal, transdermal, subcutaneous, injectable, intravenous, or intramuscular administration comprising an amount of Compound I or a pharmaceutically acceptable salt thereof, wherein the amount is from 20 to 30 mg per dose.

In one aspect, the invention relates to a pharmaceutical composition comprising an amount of Compound I or a pharmaceutically acceptable salt thereof, wherein the amount is about 10, 15, 20, 25, 30, 45 50, 60, 75, 90 or 100 mg per dose.

In one aspect, the invention relates to a pharmaceutical composition, wherein the administration of Compound I or a pharmaceutically acceptable salt thereof is intravenous.

In one aspect, the invention relates to a pharmaceutical composition, wherein the administration of Compound I or a pharmaceutically acceptable salt thereof is intravenous over time. In one aspect, the invention relates to a pharmaceutical composition, wherein the administration of Compound I or a pharmaceutically acceptable salt thereof is intravenous over a period of about 20 minutes. In one aspect, the invention relates to a pharmaceutical composition, wherein the administration of Compound I or a pharmaceutically acceptable salt thereof is intravenous over a period of 20 minutes.

In one aspect, the invention relates to a pharmaceutical composition, wherein the administration of Compound I or a pharmaceutically acceptable salt thereof is buccal.

In one aspect, the invention relates to a pharmaceutical composition, wherein the administration is sublingual.

In one aspect, the invention relates to a pharmaceutical composition, wherein the administration of Compound I or a pharmaceutically acceptable salt thereof is nasal or intranasal.

In one aspect, the invention relates to a pharmaceutical composition, wherein the administration of Compound I or a pharmaceutically acceptable salt thereof is transdermal.

In one aspect, the invention relates to a pharmaceutical composition, wherein the administration of Compound I or a pharmaceutically acceptable salt thereof is subcutaneous.

In one aspect, the invention relates to a pharmaceutical composition, wherein the administration of Compound I or a pharmaceutically acceptable salt thereof is injectable.

In one aspect, the invention relates to a pharmaceutical composition, wherein the administration is intramuscular.

The invention relates to a pharmaceutical composition, wherein the composition comprises a pharmaceutically acceptable salt of Compound I. In one aspect, the invention relates to a pharmaceutical composition, wherein the composition comprises the hemi-succinate salt of Compound I. In one aspect, the invention relates to a pharmaceutical composition, wherein the composition comprises the mono-hydrochloride salt of Compound I.

In one aspect, the invention relates to a pharmaceutical composition, wherein the dose of Compound I is administered one time daily. In one aspect, the invention relates to a pharmaceutical composition, wherein the dose of Compound I is administered two times daily. In one aspect, the invention relates to a pharmaceutical composition, wherein the dose of Compound I is administered three times daily.

The invention relates to a method for the treatment or prevention of migraine in a mammal in need thereof comprising administering to a mammal in need of such treatment or prevention an effective amount of a composition described herein. In one aspect, the invention relates to a method, wherein the mammal is a human.

The invention relates to the use of a composition described herein for the preparation of a medicament for the treatment or prevention of migraine in a mammal.

One embodiment of the present invention is a method using a composition of the invention for increasing activation of 5-HT$_{1F}$ receptors, while avoiding vasoconstrictive activity, for treating a variety of disorders that have been linked to decreased neurotransmission of serotonin in mammals. Included among these disorders are migraine, general pain, trigeminal neuralgia, dental pain or temperomandibular joint dysfunction pain, anxiety, general anxiety disorder, panic disorder, depression, disorders of sleep, fatigue syndrome, premenstrual syndrome or late luteal phase syndrome, post-traumatic syndrome, memory loss, dementia including dementia of aging, social phobia, autism, attention deficit hyperactivity disorder, disruptive behavior disorders, impulse control disorders, borderline personality disorder, obsessive compulsive disorder, premature ejaculation, erectile dysfunction, bulimia, anorexia nervosa, alcoholism, tobacco abuse, mutism, and trichotillomania. In one embodiment, the disorder is chronic. A composition of the invention is also useful as a prophylactic treatment for migraine.

In those instances where the disorders which can be treated by serotonin agonists are known by established and accepted classifications, their classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

The use of a composition of the invention for the activation of the 5-HT$_{1F}$ receptor, for the inhibition of neuronal peptide extravasation, in general or due to stimulation of the trigeminal ganglia specifically, and/or for the treatment of any of the disorders described above, are all embodiments of the present invention.

Likewise, the use of a composition of the invention in the manufacture of a medicament for the activation of the 5-HT$_{1F}$ receptor, for the inhibition of neuronal peptide extravasation, in general or due to stimulation of the trigeminal ganglia specifically, and/or for the treatment of any of the disorders described above, are also all embodiments of the present invention.

As used herein, the phrase "pharmaceutically acceptable" refers to those active compounds, materials, compositions, carriers, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The term "Compound I" or "Cmpd I" as used herein means 2,4,6-trifluoro-N-[6-(1-methyl-piperidin-4-ylcarbonyl)-pyridin-2-yl]-benzamide:

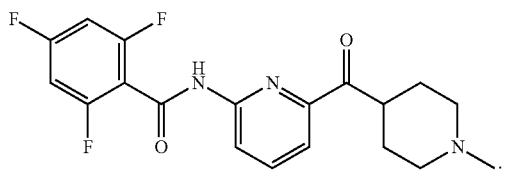 [SMILES: CN1CCC(C(=O)c2cccc(NC(=O)c3c(F)cc(F)cc3F)n2)CC1]

By "pharmaceutical formulation" it is further meant that the carrier, solvent, excipients and salt must be compatible with the active ingredient of the formulation (e.g. Compound I). It is understood by those of ordinary skill in this art that the terms "pharmaceutical formulation" and "pharmaceutical composition" are generally interchangeable, and they are so used for the purposes of this application.

The term "acid addition salt" refers to a salt of Compound I prepared by reaction of Compound I with a mineral or organic acid. For exemplification of pharmaceutically acceptable acid addition salts see, e.g., Berge, S. M, Bighley, L. D., and Monkhouse, D. C., *J. Pharm. Sci.*, 66:1, 1977. Since Compound I is an amine, it is basic in nature and accordingly reacts with any of a number of inorganic and organic acids to form an acid addition salt e.g., a pharmaceutically acceptable acid addition salt.

The pharmaceutically acceptable acid addition salts of the invention are typically formed by reacting Compound I with an equimolar or excess amount of acid. Alternatively, hemisalts can be formed by reacting Compound I with the desired acid in a 2:1 ratio, compound to acid. The reactants are generally combined in a mutual solvent such as diethylether, tetrahydrofuran, methanol, ethanol, isopropanol, benzene, toluene or the like. The salts normally precipitate out of solution within about one hour to about ten days and can be isolated by filtration or other conventional methods.

Inorganic acids commonly employed to form such salts include hydrochloric acid, hydrobromic acid, hydroiodic acid, sulfuric acid, phosphoric acid, and the like. Organic acids commonly employed to form such salts include p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, hemisuccinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid or succinic acid.

The term "effective amount" means an amount of Compound I which is capable of activating 5-HT$_{1F}$ receptors and/or inhibiting neuronal protein extravasation.

The term "suitable solvent" refers to any solvent, or mixture of solvents, inert to the ongoing reaction that sufficiently solubilizes the reactants to afford a medium within which to effect the desired reaction.

The term "prophylaxis treatment" means causing the clinical symptoms of the disorder not to develop i.e., inhibiting the onset of the disorder or a condition, in a subject that may be exposed to or predisposed to the disorder or the condition, but does not yet experience or display symptoms. In one aspect, the term "prophylaxis treatment" refers to prophylactic treatment of migraine i.e., prevention of migraine headache.

As used herein, the term "treat," "treatment," or "treating" refers to partially or completely alleviate, ameliorate, relieve, inhibit, reduce severity of, and/or reduce incidence of one or more symptoms or features of migraine.

It is preferred that the mammal to be treated by the administration of the compositions of this invention is human.

Formulations

The type of formulation used for the administration of Compound I may be dictated by the type of pharmacokinetic profile desired from the route of administration, and the state of the patient.

Formulations amenable to oral, sublingual, nasal or injectable administration are prepared in a manner well known in the pharmaceutical art and comprise at least one active compound. See, e.g., REMINGTON'S PHARMACEUTICAL SCIENCES, (16th ed. 1980).

In general, a formulation of the present invention includes an active ingredient (Compound I) and is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, gels, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh. In one embodiment of the present invention, the particle size range is between about 0.1 µm to about 100 µm.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents.

The following formulation examples are illustrative only and are not intended to limit the scope of the present invention. The term "active ingredient" refers to Compound I Formulation Example 1

| Hard Gelatin Capsules | |
|---|---|
| Ingredient | Quantity (mg/capsule) |
| 2,4,6-Trifluoro-N-[6-(1-methyl-piperidine-4-carbonyl)-pyridin-2-yl]-benzamide hydrochloric acid salt | 30.0 |
| Starch | 305.0 |
| Magnesium stearate | 5.0 |

The above ingredients are mixed and filled into hard gelatin capsules in 340 mg quantities.

Formulation Example 2

| Tablet | |
|---|---|
| Ingredient | Quantity (mg/tablet) |
| 2,4,6-Trifluoro-N-[6-(1-methyl-piperidine-4-carbonyl)-pyridin-2-yl]-benzamide hydrochloric acid salt | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

| Dry Powder Inhaler | |
|---|---|
| Ingredient | Weight % |
| 2,4,6-Trifluoro-N-[6-(1-methyl-piperidine-4-carbonyl)-pyridin-2-yl]-benzamide | 5 |
| Lactose | 95 |

The active ingredient is mixed with the lactose and the mixture is added to a dry powder inhaling appliance.

Formulation Example 4

| Tablet | |
|---|---|
| Ingredient | Quantity (mg/tablet) |
| 2,4,6-Trifluoro-N-[6-(1-methyl-piperidine-4-carbonyl)-pyridin-2-yl]-benzamide | 30.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C.-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

| Capsules | |
|---|---|
| Ingredient | Quantity (mg/capsule) |
| 2,4,6-Trifluoro-N-[6-(1-methyl-piperidine-4-carbonyl)-pyridin-2-yl]-benzamide | 40.0 |
| Starch | 109.0 |
| Magnesium stearate | 1.0 |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

| Suspensions | |
|---|---|
| Ingredient | Amount |
| 2,4,6-Trifluoro-N-[6-(1-methyl-piperidine-4-carbonyl)-pyridin-2-yl]-benzamide hydrochloric acid salt | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 7

| Capsules | |
|---|---|
| Ingredient | Quantity (mg/capsule) |
| 2,4,6-Trifluoro-N-[6-(1-methyl-piperidine-4-carbonyl)-pyridin-2-yl]-benzamide | 15.0 |
| Starch | 407.0 |
| Magnesium stearate | 3.0 |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 8

| Intravenous Formulation | |
|---|---|
| Ingredient | Quantity |
| 2,4,6-Trifluoro-N-[6-(1-methyl-piperidine-4-carbonyl)-pyridin-2-yl]-benzamide | 250.0 mg |
| Isotonic saline | 1000 ml |

Formulation Example 9

| Sublingual or Buccal Tablets | |
|---|---|
| Ingredient | Quantity (mg/tablet) |
| 2,4,6-Trifluoro-N-[6-(1-methyl-piperidine-4-carbonyl)-pyridin-2-yl]-benzamide hydrochloric acid salt | 10.0 |
| Glycerol | 210.5 |
| Water | 143.0 |
| Sodium citrate | 4.5 |
| Polyvinyl alcohol | 26.5 |
| Polyvinylpyrrolidone | 15.5 |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the active ingredient is slowly admixed. The homogenous mixture is poured into forms made of an inert material to produce a drug-containing diffusion matrix having a thickness of about 2-4 mm. This diffusion matrix is then cut to form individual tablets having the appropriate size.

Formulation Example 9

| Sublingual or Buccal Tablets | |
|---|---|
| Ingredient | Quantity (mg/tablet) |
| 2,4,6-Trifluoro-N-[6-(1-methyl-piperidine-4-carbonyl)-pyridin-2-yl]-benzamide hemi-succinnic acid salt | 5.0 (freebase equivalent) |
| Mannitol | 20 |
| Gelatine | 2.0 |
| Water add to total volume of | 100 μL |
| Total | 27.0 mg |

Compound I was dissolved in water containing 20% mannitol and 2% gelatine to provide a stock solution at a concentration of 50 mg/mL (free base equivalent). The solution was aliquoted into forms holding 100 μL solution each. The formulation was then frozen at −20° C. for 3 hours and freeze dried.

Formulation Example 8

| Intravenous Formulation | |
|---|---|
| Ingredient | Quantity per 1.0 mL Formulation |
| 2,4,6-Trifluoro-N-[6-(1-methyl-piperidine-4-carbonyl)-pyridin-2-yl]-benzamide hemi-succinnic acid salt | 1.16 mg |
| Mannitol parenteral | 50.0 mg |
| Water for injection: q.s. to | 1.0 mL |

The compound and mannitol are dissolved in water and then water is added to obtain the desired final volume. The solution is then sterile filtered and aseptically filled into suitable vials.

While it is possible to administer Compound I in the methods of this invention directly without any formulation, Compound I is usually administered in the form of a pharmaceutical formulation comprising a pharmaceutically acceptable excipient and at least one active ingredient. These formulations can be administered by a variety of routes including oral, buccal, rectal, intranasal, transdermal, subcutaneous, intravenous, intramuscular, and intranasal. Compound I is effective as both injectable and oral compositions.

In order to administer transdermally, a transdermal delivery device ("patch") is needed. Such transdermal patches may be used to provide continuous or discontinuous infusion of Compound I in controlled amounts. The construction and use of transdermal patches for the delivery of pharmaceutical agents is well known in the art. See, e.g., U.S. Pat. No. 5,023,252. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, which is herein incorporated by reference. The delivery of hydrophilic drugs may be enhanced by intra-arterial infusion of hypertonic solutions which can transiently open the blood-brain barrier.

In one aspect of the present invention, there is provided a pharmaceutical formulation comprising at least Compound I as described above in a formulation adapted for buccal and/or sublingual, or nasal administration. This embodiment provides administration of Compound I in a manner that avoids gastric complications, such as first pass metabolism by the gastric system and/or through the liver. This administration route may also reduce adsorption times, providing more rapid onset of therapeutic benefit. Compound I may provide particularly favorable solubility profiles to facilitate sublingual/buccal formulations. Such formulations typically require relatively high concentrations of active ingredients to deliver sufficient amounts of active ingredients to the limited surface area of the sublingual/buccal mucosa for the relatively short durations the formulation is in contact with the surface area, to allow the absorption of the active ingredient. Thus, the very high activity of Compound I combined with its high solubility, facilitates its suitability for sublingual/buccal formulation.

Compound I is preferably formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient as described above.

The amount of Compound I needed to be effective depends on the chosen route of administration.

EXAMPLES

The following Examples are illustrative and should not be interpreted in any way so as to limit the scope of the invention.

Example 1: Compound I Activity

Compound I is useful for increasing activation of the 5-HT$_{1F}$ receptor. An increase in the activation of the 5-HT$_{1F}$ is useful for treating a variety of disorders which have been linked to decreased neurotransmission of serotonin in mammals, e.g., migraine headaches. See U.S. Pat. No. 5,708,008 demonstrating the *nexus* between activation of the 5-HT$_{1F}$ receptor and migraine. Compound I may be prepared using methods known in the art. Preparations of Compound I are described in U.S. Pat. No. 7,423,050 and U.S. Publication No. 20080300407. To demonstrate the use of Compound I in the treatment of migraine, the ability of Compound I to bind to the 5-HT$_{1F}$ receptor subtype was determined. The ability of Compound I to bind to the 5-HT$_{1F}$ receptor subtype was measured essentially as described in N. Adham, et al., *Proceedings of the National 15 Academy of Sciences (USA)*, 90:408-412, 1993.

Membrane Preparation:

Membranes were prepared from transfected Ltk-cells (transfected with the human 5-HT$_{1F}$ receptor sequence) which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH 7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The resulting pellet was washed once in ice-cold Tris wash buffer and resuspended in a final buffer containing 50 mM Tris HCl and 0.5 mM EDTA, pH 7.4 at 23° C. Membrane preparations were kept on ice and utilized within two hours for the radioligand binding assays. Protein concentrations were determined by the method of Bradford. Anal. Biochem., 72:248-254, 1976.

Radioligand Binding:

[$^3$H] 5-HT binding was performed using slight modifications of the 5-HT$_{1D}$ assay conditions reported by Herrick-Davis and Titeler (*J. Neurochem.*, 50:1624-1631, 1988) with the omission of masking ligands. Radioligand binding studies were achieved at 37° C. in a total volume of 250 µL of buffer (50 mM Tris, 10 mM MgCl$_2$, 0.2 mM EDTA, 10 µM pargyline, 0.1% ascorbate, pH 7.4 at 37° C.) in 96 well microtiter plates. Saturation studies were conducted using [$^3$H] 5-HT at 12 different concentrations ranging from 0.5 nM to 100 nM. Displacement studies were performed using 4.5-5.5 nM [$^3$H] 5-HT. The binding profile of drugs in competition experiments was accomplished using 6-12 concentrations of compound. Incubation times were 30 minutes for both saturation and displacement studies based upon initial investigations which determined equilibrium binding conditions. Nonspecific binding was defined in the presence of 10 µM 5-HT. Binding was initiated by the addition of 50 µL membrane homogenates (10-20 µg). The reaction was terminated by rapid filtration through presoaked (0.5% polyethyleneimine) filters using 48R Brandel Cell Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H] 5-HT averaged between 45-50%. Binding data was analyzed by computer-assisted nonlinear regression analysis (Accufit and Accucomp, Lunden Software, Chagrin Falls, Ohio). IC$_{50}$ values were converted to K$_i$ values using the Cheng-Prusoff equation. *Biochem. Pharmacol.*, 22:3099-3108 (1973).

Selectivity for the 5-HT$_{1F}$ Receptor

Compound I is relatively selective for the 5-HT$_{1F}$ receptor, particularly in comparison to other 5-HT receptor subtypes, specifically other receptors in the 5-HT$_1$ subclass, as for example, but without limitation, the 5-HT$_{1A}$, 5-HT$_{1B}$, 5-HT$_{1D}$, and 5-HT$_{1E}$ receptor subtypes. Affinity for these other receptor subtypes can readily be determined by slight modification of the above described radioligand receptor binding assays using cells transfected with the desired receptor subtype in place of cells transfected with the 5-HT$_{1F}$ receptor subtype. The binding affinity of Compound I was determined by such assays and was found to be selective for the 5-HT$_{1F}$ receptor; that is the affinity of Compound I for the 5-HT$_{1F}$ receptor was on the whole, higher than for other receptor subtypes, particular for the 5-HT$_{1B}$ and 5-HT$_{1D}$ receptor subtypes.

Measurement of cAMP Formation

As was reported by R. L. Weinshank, et al., WO93/14201, the 5-HT$_{1F}$ receptor is functionally coupled to a G-protein as measured by the ability of serotonin and serotonergic drugs to inhibit forskolin stimulated cAMP production in NIH3T3 cells transfected with the 5-HT$_{1F}$ receptor. Adenylate cyclase activity was determined using standard techniques. A maximal effect is achieved by serotonin. An E$_{max}$ is determined by dividing the inhibition of a test compound by the maximal effect and determining a percent inhibition. N. Adham, et al., supra; R. L. Weinshank, et al., *Proceedings of the National Academy of Sciences (USA)*, 89:3630-3634, 1992; and the references cited therein.

Human 5-HT$_{1F}$ receptor transfected NIH3T3 cells (estimated B$_{max}$ from one point competition studies=488 fmol/mg of protein) were incubated in DMEM, 5 mM theophylline, 10 mM HEPES (4-[2-hydroxyethyl]-1-piperazineethanesulfonic acid) and 10 µM pargyline for 20 minutes at 37° C., 5% CO$_2$. Drug dose-effect curves were then conducted by adding 6 different final concentrations of drug, followed immediately by the addition of forskolin (10 µM). Subsequently, the cells were incubated for an additional 10 minutes at 37° C., 5% CO$_2$. The medium was aspirated and the reaction was stopped by the addition of 100 mM HCl. To demonstrate competitive antagonism, a dose-response curve for 5-HT was measured in parallel, using a fixed dose of methiothepin (0.32 µM). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.).

Radioactivity was quantified using a Packard COBRA Auto Gamma counter, equipped with data reduction software. Compound I was tested and found to be an agonist of the $5\text{-HT}_{1F}$ receptor in the cAMP assay described above.

Protein Extravasation Assay

The following test was performed to determine the ability of Compound I to inhibit protein extravasation, which test is also a functional assay for the neuronal mechanism of migraine.

Harlan Sprague-Dawley rats (225-325 g) or guinea pigs from Charles River Laboratories (225-325 g) were anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes were drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes, insulated except at the ends (Rhodes Medical Systems, Inc.), were lowered through the holes in both hemispheres to a depth of 9 mm (rats) or 10.5 mm (guinea pigs) from dura.

The femoral vein was exposed and a dose of Compound I was injected intravenously (1 mL/kg). Approximately 7 minutes later, a 50 mg/kg dose of Evans Blue, a fluorescent dye, was also injected intravenously. The Evans Blue complexed with proteins in the blood and functioned as a marker for protein extravasation. Exactly 10 minutes post-injection of Compound I, the left trigeminal ganglion was stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals were killed and exsanguinated with 20 mL of saline. The top of the skull was removed to facilitate the collection of the dural membranes. The membrane samples were removed from both hemispheres, rinsed with water, and spread flat on microscopic slides. Once dried, the tissues were coverslipped with a 70% glycerol/water solution.

A fluorescence microscope (Zeiss) equipped with a grating monchromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500 µm steps) on each dural sample. The mean and standard deviation of the measurements were determined by the computer.

The extravasation induced by the electrical stimulation of the trigeminal ganglion was an ipsilateral effect (i.e., occurs only on the side of the dura in which the trigeminal ganglion was stimulated). This allows the other (unstimulated) half of the dura to be used as a control. The ratio of the amount of extravasation in the dura from the stimulated side compared to the unstimulated side was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve was generated and the dose that inhibited the extravasation by 50% ($ID_{50}$) was approximated. Compound I was assayed by the above procedure and found to significantly inhibit neuronal protein extravasation.

Rabbit Saphenous Vein Contraction

Compound I was tested in a rabbit saphenous vein contraction assay to measure their ability to mediate vasoconstriction.

Male New Zealand White rabbits (3-6 lbs) (Hazleton, Kalamazoo, Mich.) were sacrificed by a lethal dose of sodium pentobarbital (325 mg) injected into the ear vein. Tissues were dissected free of connective tissue, cannulated in situ with polyethylene tubing (PESO, outside diameter=0.97 mm) and placed in petri dishes containing modified Kreb's solution (described infra). The tips of two 30-gauge stainless steel hypodermic needles bent into an L-shape were slipped into the polyetylene tubing. Vessels were gently pushed from the cannula onto the needles. The needles were then separated so that the lower one was attached with thread to a stationary glass rod and the upper one was tied with thread to the transducer.

Tissues were mounted in organ baths containing 10 mL of modified Krebs' solution of the following composition: 118.2 mMol NaCl, 4.6 mMol KCl, 1.6 mMol $CaCl_2.H_2O$, 1.2 mMol $KH_2PO_4$, 1.2 mMol $MgSO_4$, 10.0 mMol dextrose and 24.8 mMol $NaHCO_3$. Tissue bath solutions were maintained at 37° C. and aerated with 95% $O_2$ and 5% $CO_2$. An initial optimum resting force of 1 gm was applied to the saphenous vein. Isometric contractions were recorded as changes in grams of force on a Beckman Dynograph with Statham UC-3 transducers and microscale accessory attachments. Tissues were allowed to equilibrate 1 to 2 hours before exposure to drugs. Cumulative agonist concentration-response curves were generated in tissues and no tissue was used to generate more than two agonist concentration-response curves. Results are expressed as a mean $EC_{50}$ and the maximal response expressed as a percentage of the maximal tissue contraction response to 67 mM KCl administered initially to each tissue.

This vasoconstriction assay measures two important parameters, saphenous vein contraction ($EC_{50}$) and maximal contraction as a % maximal KCl response ($\%_{max}$ KCl). The saphenous vein contraction ($EC_{50}$) is a measure of the dose required to contract tissue to 50% of the maximal response that the specific compound is capable of mediating. The maximal response that the saphenous vein is capable of exhibiting is measured after administration of a high concentration (67 mM) of KCl. The % maximal KCl contraction is the ratio of the maximal response that the specific compound is capable of mediating divided by the maximal response that the tissue can produce upon stimulation with KCl. For purposes of this application, a compound may be considered to not have significant vasoconstrictive activity if it produces a maximal contraction of less than or equal to 5% of the contraction produced by the 67 mM KCl positive control at compound concentrations of up to 100 µM.

Compound I was tested with the above saphenous vein assay and found to not be significantly vasoconstrictive. This contrasts greatly with prior art compounds for the treatment of migraine targeting the neural vasoconstrictive model for migraine treatment, which compounds were selected on the basis of strong vasoconstrictive activity, as for example, sumatriptan (known migraine treatment), which has an $EC_{50}$ of 0.66 mM and a $\%_{max}$ KCl of 64.20 in this assay.

Specifidity Index

The specificity Compound I for 5-HT$_{1F}$ mediated inhibition of neuronal protein extravasation versus vasoconstrictive activity can be expressed with a Specificity Index, which is the ratio of vasoconstriction to efficacy in inhibiting neuronal protein extravasation:

$$\text{Specificity Index} = \frac{\text{Corrected Vasoconstriction } EC_{50} \text{ (M)}}{\text{Extravasation } ID_{50} \text{ (mMol/kg)}}$$

The Corrected Vasoconstriction takes into consideration the maximal contraction relative to KCl for each individual compound, and is defined as the vasoconstriction EC$_{50}$ value divided by the %$_{max}$ KCl.

For example, sumatriptan has a corrected vasoconstriction EC$_{50}$ of $1.03\times10^{-8}$ M (0.66 mM EC$_{50}$÷64.20%$_{max}$ KCl) and an extravasation inhibition ID$_{50}$ of $2.6\times10-8$ mMol/Kg, giving a Specificity Index of 0.40.

Thus, the procedure for determining the Specificity Index of any given compound is as follows:

1. Measure the affinity of the compound for the 5-HT$_{1F}$ receptor using the radioligand binding method described above;

2. Once affinity for the 5-HT$_{1F}$ receptor is established, determine whether the compound is an agonist, partial agonist or antagonist of the 5-HT$_{1F}$ receptor by its response in the above described cAMP assay;

3. If the compound is shown to be an agonist or partial agonist with an E$_{max}$ of at least about 50%, measure efficacy of the compound in inhibition of protein extravasation and saphenous vein contraction using the above described assays; and 4. Calculate the Specificity Index as shown above.

A compound with a Specificity Index greater than 1 is useful for the methods and uses of the present invention, larger values for the Specificity Index are preferred. A larger Specificity Index indicates greater specificity for efficacy in inhibition of neuronal protein extravasation over vasoconstriction.

Example 2: A Double Blind Randomized Placebo-Controlled Parallel Group

Dose-Ranging Study of Oral Compound I in the Acute Treatment of Migraine A study is conducted to evaluate the efficacy (headache response at two hours) of a range of oral doses of Compound I. A secondary objective is to explore the time course and effect of a range of dose levels of Compound I on features of the migraine including: headache response, proportion of patients pain-free, headache recurrence, nausea, photophobia, phonophobia, vomiting, disability, use of rescue medication and patient global impression. The study explores the safety and tolerability of a range of doses of Compound I in terms of adverse events, physical exam, vital signs, laboratory evaluations, and ECGs. The study protocol is outlined below:

This is a prospective randomized, double-blind, placebo-controlled dose-ranging study in subjects with migraine. Patients are asked to treat a single migraine attack with study medication at home. Each subject's study participation consists of a screening visit with a telephone contact within 5 days to confirm eligibility, a treatment period of up to 8 weeks during which the subject is asked to treat one migraine attack with a single dose of one of four dose levels of oral Compound I or placebo, and a follow-up visit within 14 days of treating an attack.

Following screening, subjects are randomly assigned to receive oral Compound I (50, 100, 200 or 400 mg) or matching placebo to use as the first treatment of a new migraine attack. Subjects are instructed not to treat an attack until their eligibility has been confirmed by phone once all screening evaluations are complete. Once eligibility is confirmed subjects are asked to treat their next migraine attack within 4 hours of its onset providing that the headache severity is at least moderate at that time and not improving. Subjects record their response over the next 48 hours using a diary card. Subjects are asked not to use rescue medication until at least 2 hours after taking the study medication. Once an attack has been treated, subjects contact the clinic to schedule a follow-up visit as soon as possible and within 14 days of treatment. Patients are allocated to one of four dose levels of Compound I or matching placebo in the ratio 1:1:1:1:1 according to a predefined randomization list. At least 340 patients treat one attack with study medication.

Criteria for Inclusion/Exclusion:

Inclusion: Subjects are included in the study only if all the following criteria are met: Patients with migraine with or without aura fulfilling the IHS diagnostic criteria 1.1 and 1.2.1(2004); History of migraine for at least 1 year; Migraine onset before the age of 50 years; History of 1-8 migraine attacks per month; Male or female patients aged 18 to 65 years; Female patients of child-bearing potential must be using a highly effective form of contraception (e.g., combined oral contraceptive, IUD, abstinence, vasectomized partner); Able and willing to give written informed consent; Able and willing to complete a migraine diary card to record details of the attack treated with study medication.

Exclusion: Subjects are excluded from the study if any of the following criteria are met: History of life threatening or intolerable adverse reaction to any triptan; Use of prescription migraine prophylactic drugs within 30 days prior to Screening Visit and during study participation; Pregnant or breast-feeding women; Women of child-bearing potential not using highly effective contraception; History or evidence of coronary artery disease, ischemic or hemorrhagic stroke, epilepsy or any other condition placing the patient at increased risk of seizures; History of hypertension (controlled or uncontrolled); History of orthostatic hypotension; Sitting BP>160 mmHg systolic or >90 mmHg diastolic on 2 repeated measurements at screening; Current use of hemodynamically active cardiovascular drugs; History within the previous 3 years or current evidence of abuse of any drug, prescription or illicit, or alcohol; Significant renal or hepatic impairment; Previous participation in this clinical trial; Participation in any clinical trial of an experimental drug or device in the previous 30 days; Any medical condition or laboratory test which in the judgment of the investigator makes the patient unsuitable for the study; Known Hepatitis B or C or HIV infection; Subjects who are employees of the sponsor; Relatives of, or staff directly reporting to, the investigator; Patients with known hypersensitivity to Compound I, other 5-HT$_{1F}$ receptor agonists or to any excipient of Compound drug product; Patients who were treated with study medication in a previous Colucid study (Patients screened but not treated under that protocol are not excluded).

Criteria for Evaluation include:

Efficacy/Pharmacodynamics: Headache severity (4 point scale: none, mild, moderate, severe); Headache recurrence within 48 hours; Presence or absence of nausea; phonophobia, photophobia, vomiting; Disability (4 point scale: none, mild, moderate, severe); Requirement for rescue medication between 2 and 48 hours (yes or no); Patient global impression (7 point scale); Time to headache relief and time to pain free Safety: Physical examination; Adverse events (spontaneously reported); Vital signs; 12-lead electrocardiograms; Clinical laboratory parameters; Statistical Analysis Efficacy:

This multi-center, randomized, double-blind, parallel-group, placebo-controlled clinical study is designed to evaluate the efficacy and safety of oral Compound I in the acute treatment of migraine. The proportion of subjects with headache relief 2 hours post dose is the primary efficacy parameter. The primary efficacy analysis tests the null hypothesis that the proportions of subjects with headache relief 2 hours post dose are the same in the five study arms, versus the alternative hypothesis of a positive linear trend in the response rates, using the Cochran-Armitage test for trend. The primary analysis is performed in the modified intent-to-treat population, defined as all subjects who treat an attack with study medication, using a one-sided test at the 5% level of significance. Patients who fail to document headache severity at 2 hours or use of rescue medication before that time point are excluded from the analysis set.

Using a logistic regression model including the data from all five treatment groups, additional efficacy analyses compare each active dose group to the placebo group. Additional analyses are also be based on a per-protocol set of subjects. No interim analysis is planned.

The sample size was estimated assuming a response rate of 40% in the placebo arm and a 65% rate in the highest active dose arm. Assuming that the treatment groups are equally spaced and that the response odds ratios are equal between pairs of adjacent dose groups, the required sample size was estimated using the approach of Nam (1987). Based on 1:1:1:1:1 randomization, a total sample size of 330 patients (66 per group) is required for 90% power, based on a one-sided test at the 5% level of significance.

Safety:

Adverse events are summarized, and event rates are presented by treatment group. Laboratory data is summarized by treatment group in terms of change from baseline status.

Example 3: Acute Treatment of Migraine with Compound I by Intravenous Administration Compound I is a novel, highly selective and potent agonist at 5-HT$_{1F}$ receptors that lacks vasoconstrictor activity. Preclinical and early clinical experiments predict acute anti-migraine efficacy of Compound I that is mediated through a non-vascular, primarily neural, mechanism. In a multi-centre, placebo-controlled, double-blind, group-sequential, adaptive treatment-assignment, proof-of-concept and dose-finding study, 130 patients were treated in-hospital during a migraine attack. Patients were allocated to an intravenous dose level of Compound I or placebo in small cohorts. The starting dose was 2.5 mg. Subsequent doses were adjusted, up or down, according to the safety and efficacy seen in the preceding cohort. The primary outcome measure was headache response defined as improvement from moderate or severe headache at baseline to mild or no headache at 2 hours post-dose. The study was designed to explore the overall dose response relationship but was not powered to differentiate individual doses from placebo, nor to detect effect differences for other migraine symptoms.

Forty two patients received placebo and 88 received Compound I in doses of 2.5 to 45 mg. Patients were observed in the clinic for 4 hours after treatment and used a diary card to record symptoms and adverse events for up to 24 hours. The study was terminated when the 20 mg dose met predefined efficacy stopping rules. Fifty-four to 75% of patients treated in the 10, 20, 30 and 45 mg Compound I dose groups showed a 2 h headache response, compared to 45% in the placebo group (p=0.0126 for the linear association between response rates and dose levels). Patient global impression at 2 h and lack of need for rescue medication also showed statistically significant linear correlations with dose.

Compound I was generally well tolerated. Adverse events were reported by 65% of patients on Compound I and by 43% on placebo and were generally mild. Dizziness, paresthesiae and sensations of heaviness (usually limb) were more common on Compound I. At intravenous doses of 20 mg and higher, Compound I proved effective in the acute treatment of migraine. Without wishing to be bound by theory, the non-vascular, neural mechanism of action of Compound I may offer an alternative means to treat migraine especially in patients who have contraindications for agents with vasoconstrictor activity.

Methods

The present study was a multinational, multi-center clinical trial conducted at 11 sites in Germany, 4 in Finland, and 3 in the Netherlands. The study was conducted in accordance with the Declaration of Helsinki and internationally accepted standards of Good Clinical Practice. Prior to initiation it was approved by the relevant regulatory authorities and independent ethics committees. All subjects gave written informed consent. The clinicaltrials.gov identifier is NCT00384774.

Study Design

The study used a prospective, randomized, double-blind, placebo-controlled design with group-sequential adaptive-treatment assignment (Olesen J et al., N Engl J Med 2004: 350: 1104-10; Hall D B et al., Contemporary Clinical Trials 2005; 26: 349-63). Patients were allocated to a dose level of Compound I in small cohorts, with the first 20 cohorts consisting of 6 patients (4 received Compound I and 2 placebo) and subsequent cohorts of 5 patients (4 Compound I and 1 placebo). The first cohort was allocated to the 2.5 mg dose level. The dose used in subsequent cohorts depended on the headache response (moderate or severe headache reduced to mild or none at 2 hours) of the previous cohort: if 2 or less of the 4 active-treated patients had responded, the dose was increased, and if 3 or more of the 4 active-treated patients had responded, the dose was reduced. The dose adjustment rules were chosen to identify doses of Compound I with efficacy similar to or better than an oral triptan. This dose escalation or reduction sequence would be modified if 2 or more active-treated patients in any cohort experienced a severe non-serious adverse event, in which case the dose would be reduced for the next cohort irrespective of the response rate. The occurrence of a drug-related serious adverse event would lead to automatic suspension of the randomization pending a safety review. The lowest permissible dose of Compound I was 1 mg and the highest was 60 mg. Doses of above 60 mg of Compound I or a pharmaceutically acceptable salt thereof that are administered intravenously over 20 minutes are not well tolerated.

The up-and-down dose adjustment process was terminated with the selection of an effective dose when the following criteria had been met: at least 5 blocks of patients had been treated at this dose, and for at least 4 blocks the decision rule called for a dose decrease. Alternatively, the dose selection process could have been terminated, without the selection of an effective dose, if 5 consecutive blocks of patients had been treated at the top dose with the escalation rules calling for a dose increase each time.

Patient Screening and Selection

Patients were initially screened for eligibility at an outpatient visit outside a migraine attack, and were invited to return to the clinic for treatment with study medication of a new, moderate or severe migraine attack within 4 hours of onset. On return to the clinic, eligibility for the study was reconfirmed and the patient was randomized. Patients were eligible for the study if they were between 18 and 65 years of age and had at least a 1 year history of migraine with or without aura fulfilling the IHS diagnostic criteria 1.1 and 1.2.1 (2004), with a migraine onset before the age of 50 years (Headache Classification Subcommittee of the International Headache Society. The International Classification of Headache Disorders (second edition). Cephalalgia 2004: 24; Supp11:1-160). Patients had to be experiencing between 1 and 8 migraine attacks a month and not be using migraine prophylactic medication. Patients were in good general health and had no evidence of vascular disease or hypertension. Patients with previous intolerance of triptans were excluded. Pregnant or breast-feeding women were excluded, as were women of childbearing potential who were not using a highly reliable form of contraception.

Study Procedures

On return of the patient to the clinic, instructions for dilution of study drug were obtained from an online randomization system by a pharmacist or other study personnel, independent of the investigator, and the study drug for infusion was prepared. Both investigator and pharmacist were blinded with regard to active or placebo and only the pharmacist knew the dilution. All patients received a 60 ml intravenous infusion over 20 minutes. Efficacy and safety data before and after administration of study drug were entered immediately into an electronic data capture system, so allowing the headache response to be used to drive dose-allocation for subsequent cohorts.

After baseline assessments were completed, Compound I or placebo was infused intravenously over 20 minutes and the patient was monitored for safety and efficacy for at least 4 hours. Data were entered concurrently into an online electronic data capture system. Patients were discharged from the clinic after 4 h and continued to record migraine symptoms and adverse events until 24 h using a diary card.

Symptom Evaluation

A number of different symptoms were evaluated. The severity of headache was measured on a four point scale with 0=no pain, 1=mild pain, 2=moderate pain, 3=severe pain. Associated symptoms (nausea, vomiting, photophobia, phonophobia) were recorded as present or absent. Disability was documented on a four point scale with 0=no disability, 1=mild disability, 2=moderate disability, 3=severe disability. Data for the patient global impression was collected on a seven point scale with 1=very much better, 2=much better, 3=a little better, 4=no change, 5=a little worse, 6=much worse, 7=very much worse.

The primary efficacy measure was headache response, defined as a reduction in headache severity from moderate or severe at baseline to mild or no headache at 2 hours after initiation of infusion of study drug (HIS Clinical Trials Subcommittee. Guidelines for Controlled Trials in Migraine: second edition, Cephalalgia 2000: 20: 765-786). The secondary efficacy measures were: rates of headache response at 10 min, 20 min, 40 min, 60 min, 90 min, 180 min, and 240 min after initiation of study drug infusion; rates of headache free (reduction from moderate or severe headache at baseline to no headache pain) at 10 min, 20 min, 40 min, 60 min, 90 min, 120 min, 180 min, and 240 min after initiation of study drug; rates of sustained response, defined as a moderate or severe headache at baseline which became mild or no headache at 2 h after initiation of study drug and which did not recur (become moderate or severe) within 24 h of initiation of study drug; rates of sustained pain-free, defined as a moderate or severe headache at baseline which became no headache at 2 h after initiation of study drug and which did not recur (become mild, moderate or severe) within 24 h of initiation of study drug; presence of nausea, vomiting, photophobia and phonophobia, and degree of clinical disability throughout the study course; proportion of patients using rescue medication between 2 and 24 h after initiation of study drug, and patient global impression 2 h after initiation of study drug.

Statistical Methods

The target sample size of at most 160 patients, with at least 20 patients treated with an effective dose level and at least 10 patients treated with placebo, was selected to provide appropriate preliminary data on which to choose a dose range for further evaluation. The statistical properties of the hypothesis tests to compare one or more dose levels to placebo when doses are allocated using the group sequential adaptive treatment assignment design were not known. Formal statistical tests were therefore not used to declare the study to be "positive" or "negative" and the study was not powered for statistical significance. Furthermore, the sample size was not powered for statistical considerations.

At the conclusion of the study, the headache response rates were summarized by dose level. The Mantel-Haenszel test was used to test for a dose-response relationship. Since the study terminated due to selection of an effective dose, Fisher's exact test was used to compare the headache response rates for the selected dose versus placebo. In all analyses, the results for each dose level (including placebo) were combined across all blocks where that dose was used.

All patients who received any study medication were included in the analysis population. The patients were analyzed according to the treatment and dose level they actually received which was in every case that to which they were randomized. Missing values were not replaced.

Patient Population

In total 372 patients were screened at 18 centers in Finland, Germany and The Netherlands and 130 returned for treatment in the clinic. These 130 patients made up the analysis population. The treatment groups were generally well matched for demographic and baseline characteristics for the analysis population (Table 1).

TABLE 1

Patient demographics and background characteristics: Analysis population

| | | Compound I | | | | | | |
|---|---|---|---|---|---|---|---|---|
| | Placebo N (%) | 2.5 mg N (%) | 5 mg N (%) | 10 mg N (%) | 20 mg N (%) | 30 mg N (%) | 45 mg N (%) | Total N (%) |
| Sex: | | | | | | | | |
| Male | 4 (9.5) | 1 (25.0) | 2 (25.0) | 3 (12.5) | 4 (14.3) | 2 12.5) | 1 (25.0) | 13 (14.8) |
| Female | 38 (90.5) | 3 (75.0) | 10 (83.3) | 21 (87.5) | 24 (85.7) | 14 (87.5) | 3 (75.0) | 75 (85.2) |
| Ethnicity: | | | | | | | | |
| Caucasian | 42 (100.0) | 4 (100.0) | 11 (91.7) | 20 (83.3) | 28 (100.0) | 16 (100.0) | 4 (100.0) | 83 (94.3) |
| Non-Caucasian | 0 | 0 | 1 (8.3) | 4 (16.7) | 0 | 0 | 0 | 5 (5.6) |
| Mean age (years) | 40.3 | 46.8 | 39.2 | 34.2 | 38.9 | 40.3 | 40.8 | 38.4 |
| Migraine History: | | | | | | | | |
| Mean monthly frequency of attacks | 3.3 | 5.5 | 3.8 | 3.3 | 3.3 | 3.5 | 2.8 | 3.5 |
| Mean duration migraine history(years) | 21.2 | 30.1 | 18.2 | 17.9 | 20.5 | 21.6 | 16.4 | 19.9 |
| Current smokers | 7 (16.7) | 0 | 2 (16.7) | 0 | 7 (25.0) | 4 (25.0) | 1 (25.0) | 14 (15.9) |

1N for each dose group: 2.5 mg: 4; 5 mg: 12; 10 mg: 24; 20 mg: 28; 30 mg: 16; 45 mg: 4.

The majority of patients were female in both treatment groups: ratio F:M for Compound I 6:1, and for placebo 10:1. The majority of patients were Caucasian in both treatment groups (Compound I 94.3%, placebo 100.0%). Patients were between 19 and 63 years old, with a mean age of 38.4 years in the Compound I group and 40.3 years in the placebo group. The sequence of patient allocation to treatment groups is shown in FIG. 1.

Efficacy

Figure 2:
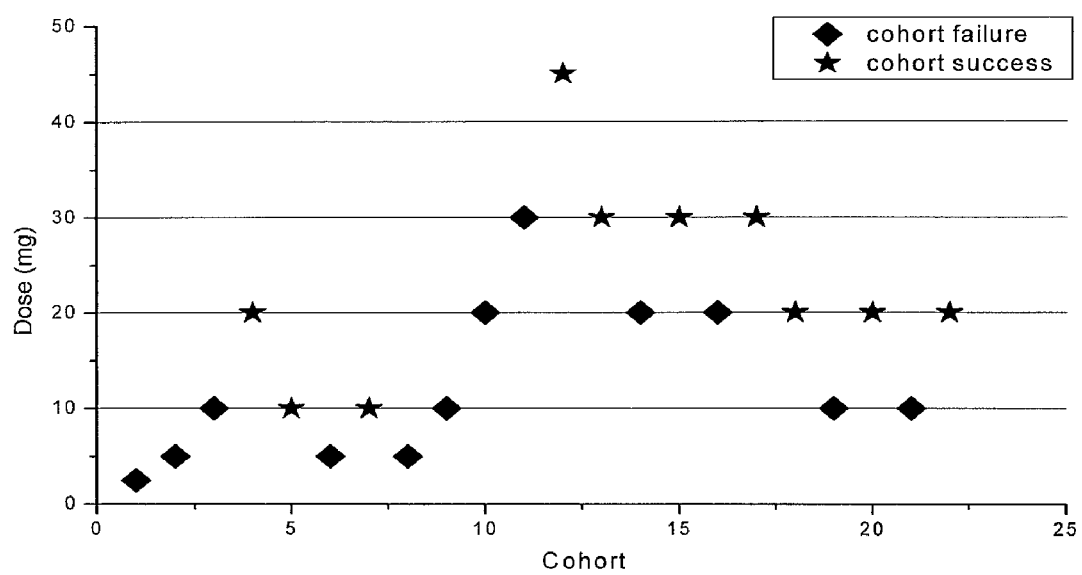
FIG. 2 is a graph that shows the dose escalation sequence of Compound I.
Figure 3:
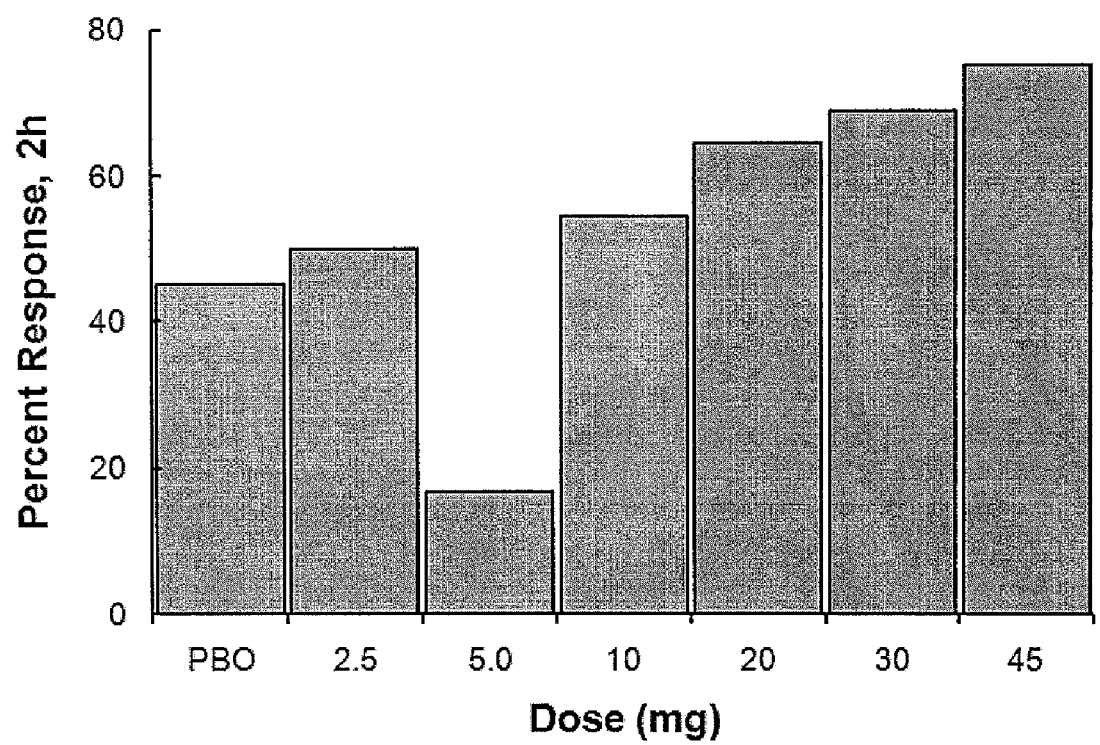
FIG. 3 is a bar graph that shows the proportion of patients with a headache response at 2 hours following administration of Compound I.
Figures 4A, 4B:
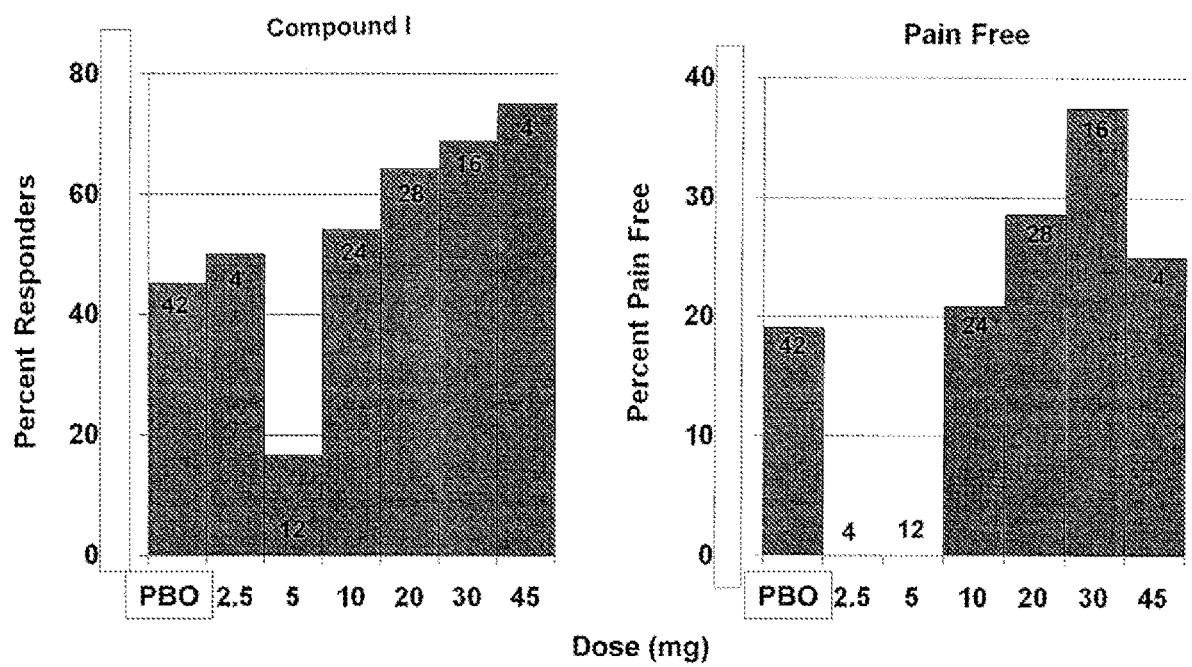
FIGS. 4A and 4B are two bar graphs that show migraine relief following iv administration of Compound I after 2 hours. In addition to headache relief at 2 hours, 30 mg iv over 20 minutes completely abolishes headache ('pain free') in a greater number of patients than placebo.

The dose escalation was terminated after 130 patients, when the predefined stopping rules identified 20 mg as an effective dose based on the results for the primary endpoint (FIGS. 2 and 3). A higher proportion of patients showed a 2 h headache response in the 10 mg, 20 mg, 30 mg, and 45 mg Compound I dose groups (54.2% to 75%) compared to placebo (45.2%) (FIG. 3). The linear association between response rate and dose level was statistically significant (p=0.0126; Mantel-Haenszel test for trend). Due to insufficient power for comparing individual dose levels, no individual Compound I dose was statistically significantly different from placebo at the 2 h time point (Fisher's exact test). A similar trend for increasing efficacy with increasing dose was observed (though not statistically tested) for headache freedom at 2 h post dose. In line with these findings, the proportion of patients using rescue medication showed an inverse trend with dose.

Table 2 shows the proportion of patients in each group who achieved a headache response at time points from 10 min to 4 h. Doses of 20 mg and above start to separate from placebo as early as 20 min after the start of the infusion.

TABLE 2

Proportion of Patients with headache response (moderate or severe predose becoming mild or none) 10 to 240 minutes post dose.

| | | Percent of Patients at Each | | | | | |
|---|---|---|---|---|---|---|---|
| | | | | Compound I | | | |
| Time | Placebo | 2.5 mg | 5 mg | 10 mg | 20 mg | 30 mg | 45 mg |
| 10 | 11.9 | 0.0 | 8.3 | 8.3 | 14.3 | 12.5 | 75.0* |
| 20 | 26.2 | 0.0 | 16.7 | 25.0 | 39.3 | 50.0 | 75.0 |
| 40 | 35.7 | 0.0 | 25.0 | 37.5 | 50.0 | 75.0* | 75.0 |
| 60 | 33.3 | 50.0 | 25.0 | 50.0 | 53.6 | 75.0* | 50.0 |
| 90 | 47.6 | 50.0 | 25.0 | 45.8 | 53.6 | 68.8 | 75.0 |
| 120 | 45.2 | 50.0 | 16.7 | 54.2 | 64.3 | 68.8 | 75.0 |
| 180 | 33.3 | 50.0 | 25.0 | 54.2 | 60.7* | 68.8* | 75.0 |
| 240 | 31.0 | 75.0 | 33.3 | 54.2 | 57.1* | 68.8* | 25.0 |

*p-value = 0.048 (20 mg/180 min), 0.048 (20 mg/240 min), 0.009 (30 mg/40 min), 0.007 (30 mg/60 min), 0.036 (30 mg/180 min), 0.017 (30 mg/240 min), 0.014 (45 mg/10 min), Fisher's exact test, dose group versus placebo.

1N for each dose group: 2.5 mg: 4; 5 mg: 12; 10 mg: 24; 20 mg: 28; 30 mg: 16; 45 mg: 4.

Table 3 summarizes the main secondary efficacy parameters. Patient global impression at 2 h and use of rescue medication up to 24 h showed significant correlations with dose (p=0.0001 and p=0.006 respectively).

TABLE 3

Secondary Efficacy Parameters

Percent of Patients at Each Dose

|  | Placebo | Cmpd I 2.5 mg | Cmpd I 5 mg | Cmpd I 10 mg | Cmpd I 20 mg | Cmpd I 30 mg | Cmpd I 45 mg |
|---|---|---|---|---|---|---|---|
| Pain freedom 2 h | 19.0 | 0.0 | 0.0 | 20.8 | 28.6 | 37.5 | 25.0 |
| Sustained pain response | 31.0 | 50.0 | 8.3 | 33.3 | 35.7 | 56.3 | 25.0 |
| Sustained pain free | 16.7 | 0.0 | 0.0 | 12.5 | 17.9 | 18.8 | 25.0 |
| Nausea 2 h | 16.7 | 25.0 | 41.7 | 12.5 | 21.4 | 6.3 | 25.0 |
| Photophobia 2 h | 50.0 | 25.0 | 75.0 | 45.8 | 42.9 | 25.0 | 25.0 |
| Phonophobia 2 h | 42.9 | 25.0 | 41.7 | 25.0 | 25.0 | 25.0 | 25.0 |
| No/mild disability 2 h | 50.0 | 75.0 | 16.6 | 54.2 | 57.1 | 75.1 | 25.0 |
| Use of rescue medication, 2-24 h | 69.0 | 25.0 | 91.7 | 58.3 | 53.6 | 37.5 | 25.0 |
| Impression: very much/much better 2h | 28.6 | 75.0 | 8.3 | 37.5 | 42.9 | 68.8 | 50.0 |

1N for each dose group: 2.5 mg: 4; 5 mg: 12; 10 mg: 24; 20 mg: 28; 30 mg: 16; 45 mg: 4.

Tolerability and Safety

Compound I was generally well tolerated with no serious adverse events or withdrawals due to non-serious adverse events. The most prominent adverse event was paresthesia which was usually mild and transient, resolving rapidly after cessation of the intravenous infusion (Table 4). Heaviness and fatigue also appeared to be dose related. No patient reported triptan-like chest symptoms in relation to the Compound I infusion. No clinically significant changes were seen in vital signs or ECG parameters or in hematological or clinical chemistry parameters.

cally relevant doses, the results of this study confirm that vasoconstriction may not be a prerequisite for antimigraine efficacy as has been suggested earlier (Goldstein D J et al., Lancet 2001; 358: 1230-4; Ho T W et al., Lancet 2008; 372: 2115-2123). One aspect of the present invention includes the treatment and prevention of migraine in the particular subpopulation of patients who cannot tolerate, or have contraindications for, triptans.

Compound I was well tolerated. There were no clinically significant abnormalities of any safety parameters, i.e. heart rate, blood pressure, 12-lead ECG, hematology, biochemistry and urine analysis, following administration of Compound I. No patient terminated treatment because of side effects. There were also no patient-reported chest symptoms or chest discomfort.

TABLE 4

Incidence of Patients with Adverse Events Preferred by Term (frequency ≥5% in either placebo or total Compound I group.

|  | Placebo N (%) | Cmpd I 2.5 mg N (%) | Cmpd I 5 mg N (%) | Cmpd I 10 mg N (%) | Cmpd I 20 mg N (%) | Cmpd I 30 mg N (%) | Cmpd I 45 mg N (%) | Total N (%) |
|---|---|---|---|---|---|---|---|---|
| Dizziness | 6 (14.3) | 2 (50.0) | 1 (8.3) | 8 (33.3) | 7 (25.0) | 3 (18.8) | 1 (25.0) | 22 (25.0) |
| Paresthesia | 0.0 | 0.0 | 0.0 | 5 (20.8) | 8 (28.8) | 7 (43.8) | 1 (25.0) | 21 (23.9) |
| Fatigue | 4 (9.5) | 0.0 | 1 (8.3) | 1 (4.2) | 5 (17.9) | 3 (18.8) | 0.0 | 10 (11.4) |
| Sensation of heaviness | 0.0 | 0.0 | 0.0 | 2 (8.3) | 3 (10.7) | 4 (25.0) | 0.0 | 9 (10.2) |
| Feeling of relaxation | 0.0 | 0.0 | 0.0 | 0.0 | 2 (7.1) | 3 (18.8) | 0.0 | 5 (5.7) |

1N for each dose group: 2.5 mg: 4; 5 mg: 12; 10 mg: 24; 20 mg: 28; 30 mg: 16; 45 mg: 4.

The acute antimigraine efficacy of Compound I was tested. Its effect is most likely mediated through a primarily neural and non-vascular mechanism. A relatively novel up-and-down dose-adaptive study design was used to minimize patient exposure to study drug or placebo while still rapidly and reliably screening for efficacy and tolerability across a wide dose range. A clear dose-related efficacy of Compound I was found in the acute treatment of a migraine attack. The onset of headache relief was evident at 20 to 40 min after the start of a 20 min intravenous infusion. As Compound I is devoid of vasoconstrictor activity at clinically relevant doses.

The 20 mg and higher doses of Compound I were identified as doses of interest for further evaluation. PK/PD modeling using pharmacokinetic data from this study will facilitate the selection of an active dose range for evaluation when given by non-parenteral routes of administration.

This study had a high placebo response rate, which is most likely due to the conditions under which the trial was conducted. Attendance at the clinic for treatment may have heightened patient expectations and trials involving parenteral administration of acute anti-migraine therapies have historically often demonstrated higher placebo rates than those in which the drug was given orally (Diener H C et al., Cephalalgia 2008; 28:1003-1011).

An adaptive design was used to identify the lowest effective dose. This is achieved with minimal patient exposure to ineffective low doses compared to a parallel group design, where the distribution of patients to dose groups is predefined. Furthermore, choice of a low starting dose and gradual escalation with ongoing safety monitoring ensured that risk to the patients was minimized.

Further data from this study is shown in FIGS. 4-9. FIGS. 4A and 4B show that in addition to headache relief at 2 hours after iv administration of Compound I, 30 mg iv over 20 minutes completely abolished headache in a greater number of patients than placebo ('pain free'). The numbers in bars are N treated at each dose.

Figure 5:
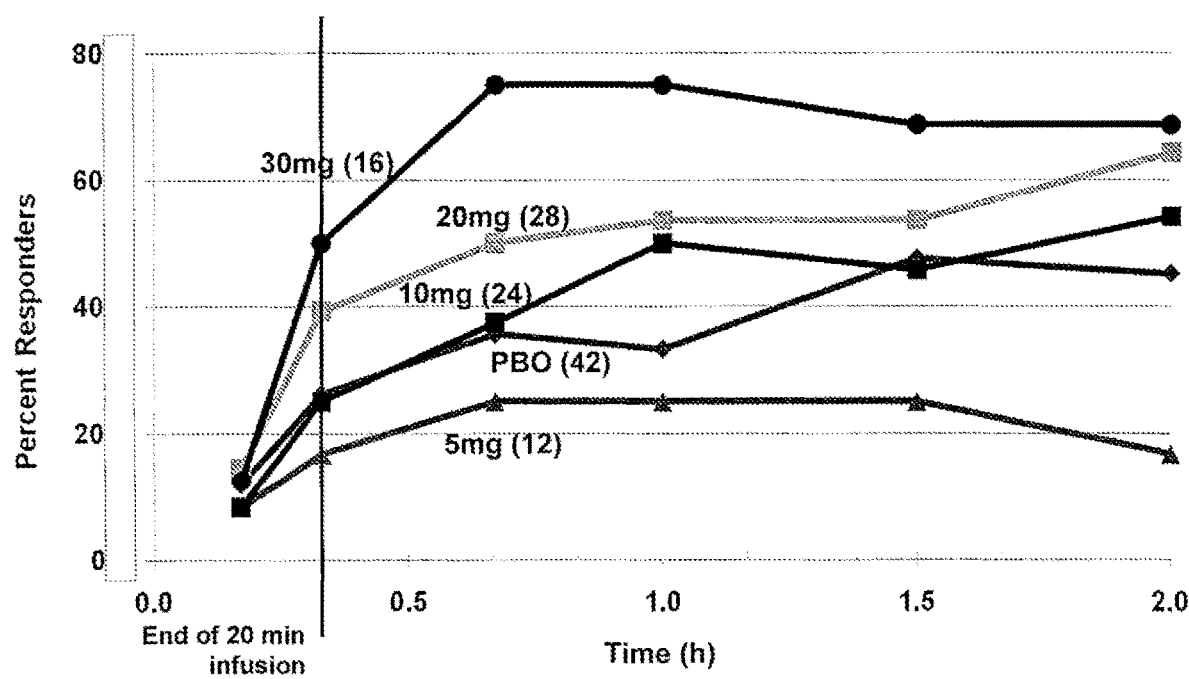
FIG. 5 is a graph that shows time course of response for Compound I administered by iv. 20 mg and 30 mg iv gave a rapid onset of headache relief.

FIG. 5 is a time course of response which shows that 20 and 30 mg iv gave a speed onset of headache relief.

Figures 6A, 6B:
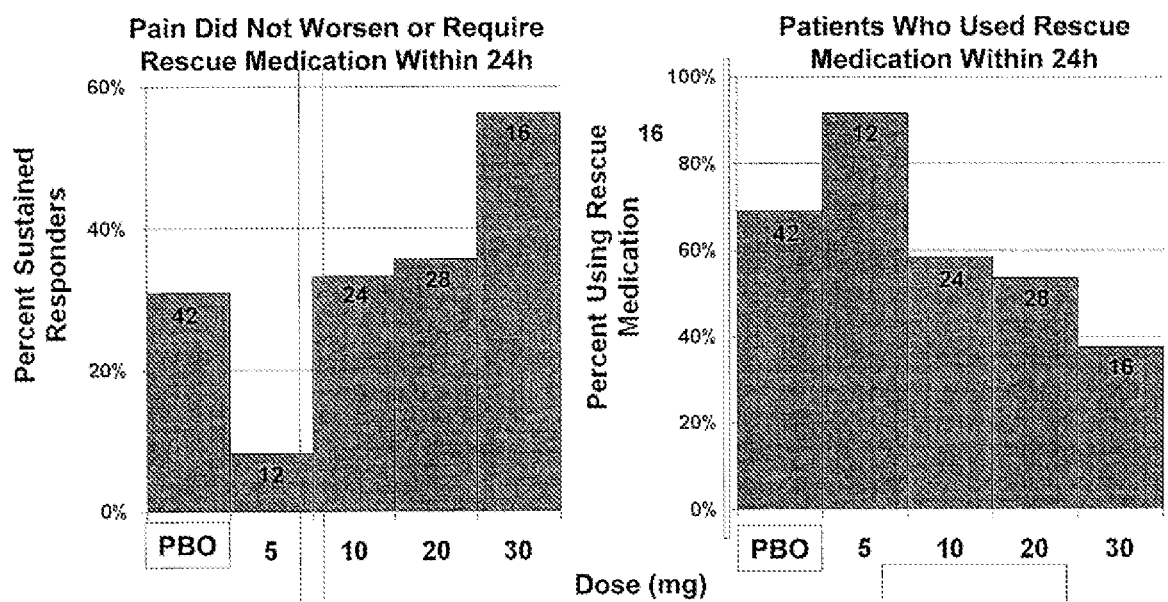
FIGS. 6A and 6B are two bar graphs that show sustained pain response with Compound I administered by iv and rescue medication results. 30 mg iv reduced headache recurrence within 24 hours and reduced the use of rescue medication.

FIGS. 6A and 6B show intravenous administration of Compound I sustained pain response and rescue medication. FIG. 6A shows pain did not worsen or require rescue medication within 24 hours. FIG. 6B shows patients who used rescue medication within 24 hours. The administration of 30 mg iv reduced headache recurrence within 24 hours and reduced the use of rescue medication. These results show potential for superior sustained response by oral route.

Figure 7:
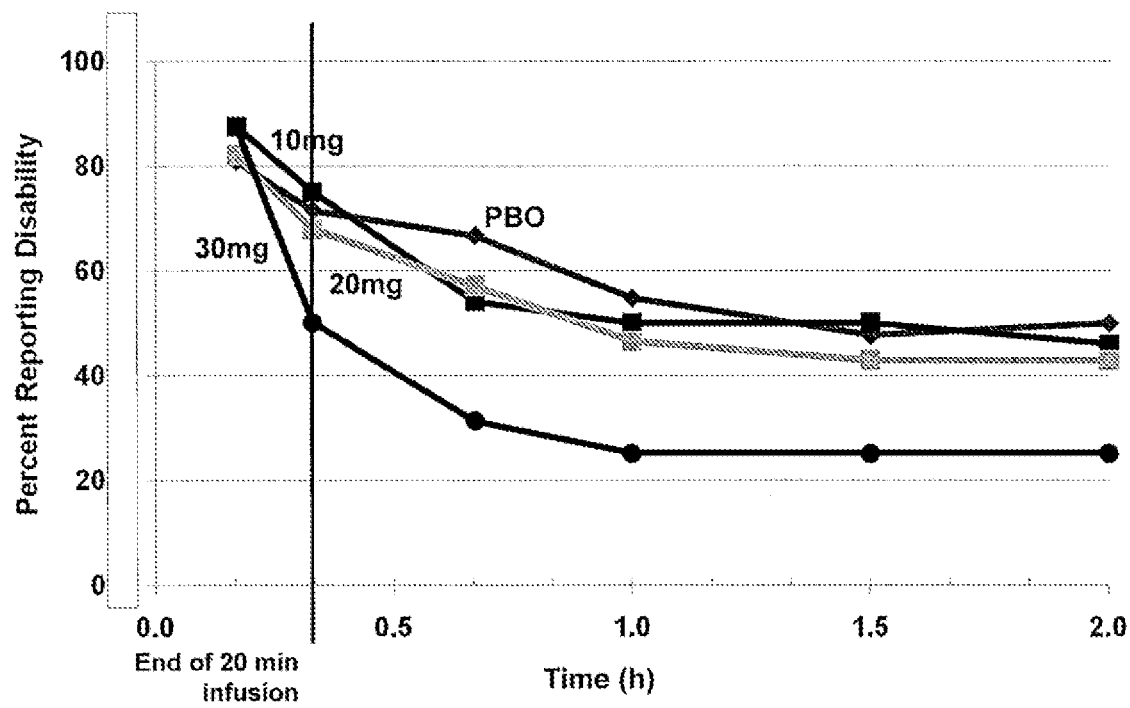
FIG. 7 is a graph that shows the percent of patients reporting moderate or severe disability after administration of Compound I following iv administration (20 min infusion).

FIG. 7 shows the percent reporting disability following intravenous administration of Compound I. The administration of 30 mg iv of Compound I reduced the percent of moderate or severe disability reported.

Figure 8:
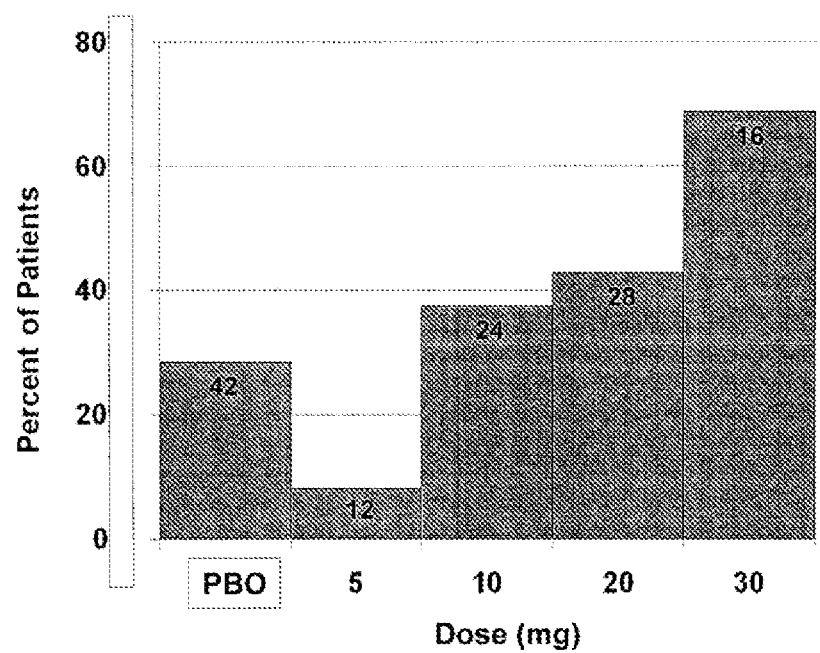
FIG. 8 is a bar graph that shows global impressions of how patients were feeling 2 hours after intravenous administration of Compound I. The 30 mg dose showed an increase in the number of patients who felt much better or very much better.

FIG. 8 shows patient global impressions following iv administration of Compound I. Specifically, FIG. 8 shows the percent of patients who reported feeling "very much" or "much better" 2 hours post dose. Numbers in bars are N treated at each dose. The administration of 30 mg iv of Compound I increased the number of patients who felt much or very much better.

Figure 9:
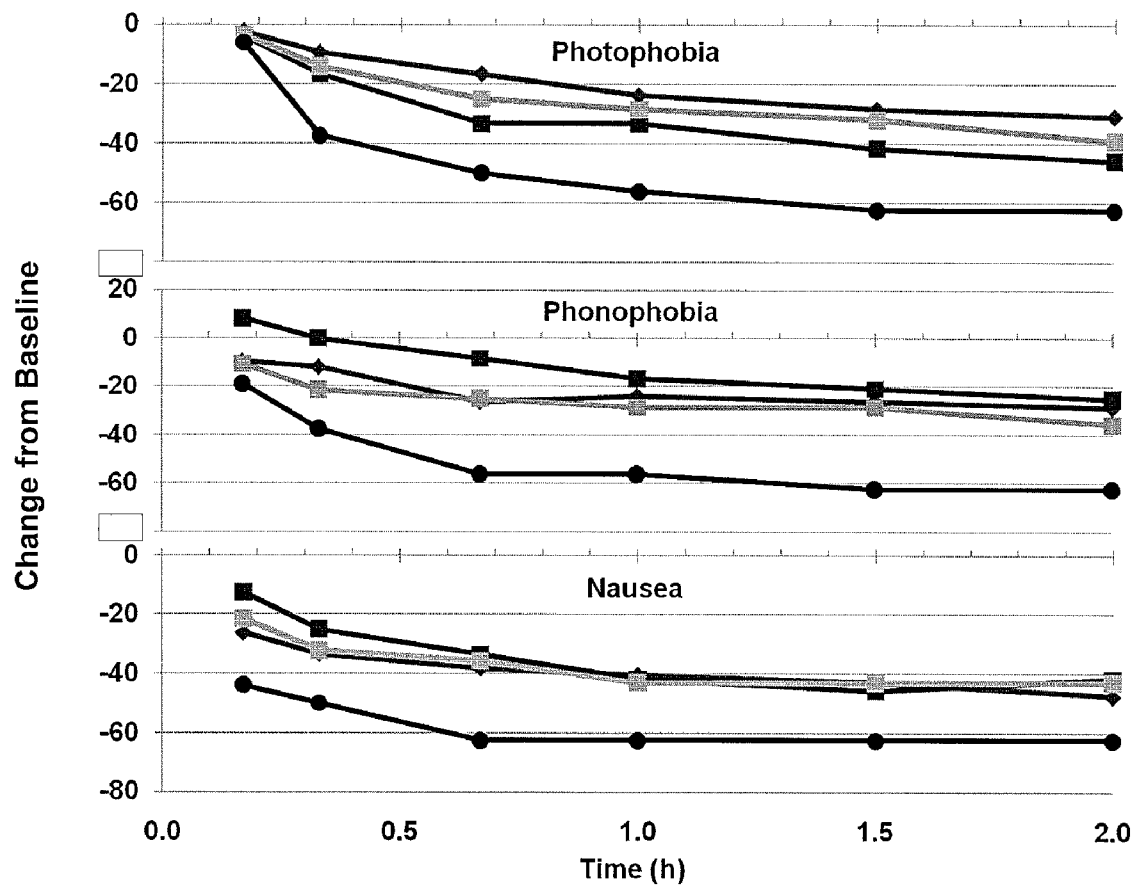
FIG. 9 is a series of graphs that show secondary endpoints following iv administration of Compound I at 10, 20, and 30 mg. The 30 mg dose reduced associated symptoms of photophobia, phonophobia, and nausea.
Figure 9:

FIG. 9 shows secondary endpoints (photophobia, phonophobia, and nausea) for intravenous administration of Compound I. The administration of 30 mg iv reduced associated symptoms of photophobia, phonophobia, and nausea.

Example 4: Safety, Tolerability, and Pharmacokinetics of Compound I Given Orally The objectives of this study include 1) to assess the safety, tolerability, and pharmacokinetics of oral Compound I over the ranges of 25-400 mg using a solution to avoid solid-formulation dependent effects; 2) to assess the relative bioavailability of tablet formulation compared to the oral solution; 3) to assess the pharmacokinetics of a tablet formulation of Compound I over the range of 50-400 mg; 4) to compare the safety, tolerability, and pharmacokinetics of a tablet formulation of Compound I in healthy males and females.

The studies were conducted in accordance with the Declaration of Helsinki and intentionally accepted standards of Good Clinical Practice. Prior to initiation the study was approved by the German regulatory authority and independent ethics committee. All subjects gave written informal consent.

Study Designs

Study 1—Placebo-controlled, randomized, dose escalation of single oral solution doses of 25-400 mg Compound I in 30 healthy male subjects.

Study 2-Part 1 is a double-blinded, randomized, double-dummy comparison of 200 mg Compound I given as an oral solution and as a tablet formulation; 28 healthy male subjects received in crossover fashion the oral solution and the tablet on 2 separate dosing days. Part 2 is a double-blinded randomized dose comparison; 14 male subjects (13 from Part 1 and 1 new subject) and 14 healthy females received 50 mg and 400 mg of Compound I as tablets in crossover fashion on 2 separate dosing days. Doses of Compound I or a pharmaceutically acceptable salt thereof above 400 mg administered orally are not well tolerated.

Safety Evaluations

Safety and tolerability of Compound I given orally were assessed in both studies by means of: adverse events, vital signs, 12-lead digital ECGs and haematology, clinical chemistry, and renal markers Pharmacokinetic Analysis Plasma samples were analyzed for Compound I using a validated liquid chromatography with tandem mass spectrometric detection (LC/MS/MS) method. Relative bioavailability of tablet and solution formulations for $AUC_t$, $AUC_\infty$, and $C_{max}$ were assessed. A linear mixed effects model was fitted to the log-transformed PK parameters ($AUC_t$, $AUC_\infty$, and $C_{max}$). Included in the model were treatment, period, and sequence as fixed factors and subjects nested within sequences as a random factor. For the relative bioavailability analysis, the tablet formulation was the test and the solution formulation was the reference. 90% confidence intervals and ratios for the relative mean in-transformed $AUC_t$, $AUC_\infty$, and $C_{max}$ of the test to reference formulation were calculated.

Results: Pharmacokinetics

Figure 10:
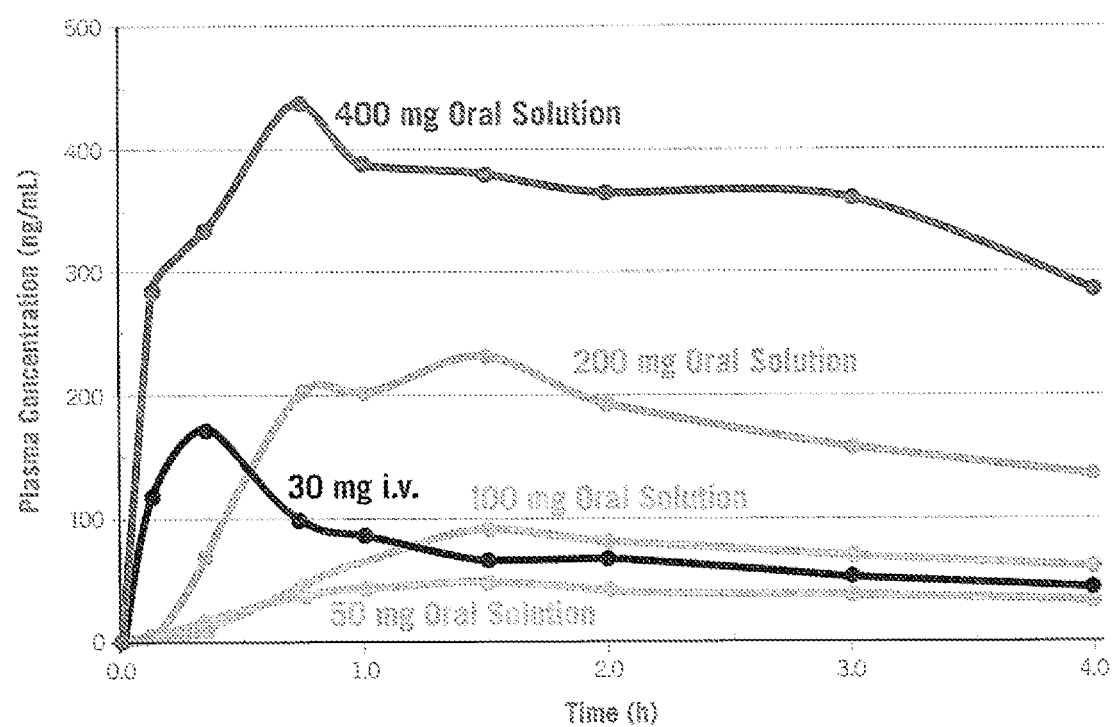
FIG. 10 is a graph that shows plasma-concentration time profiles for the 50-400 mg oral solution doses of Compound I and the 30 mg iv infusion.
Figure 11A:
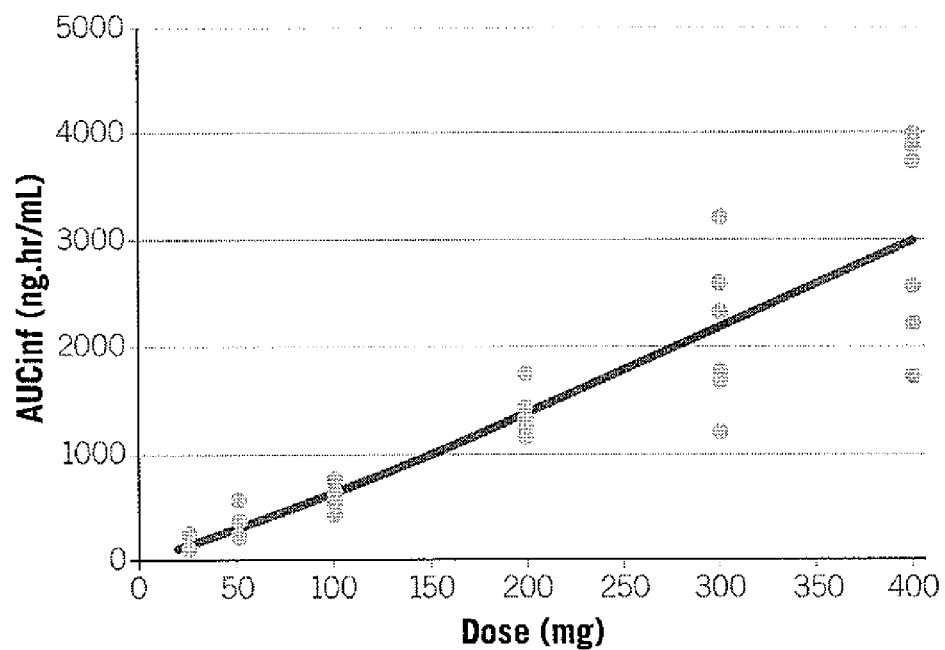
FIGS. 11A and 11B are two graphs that show dose linearity of Compound I.
Figure 11B:
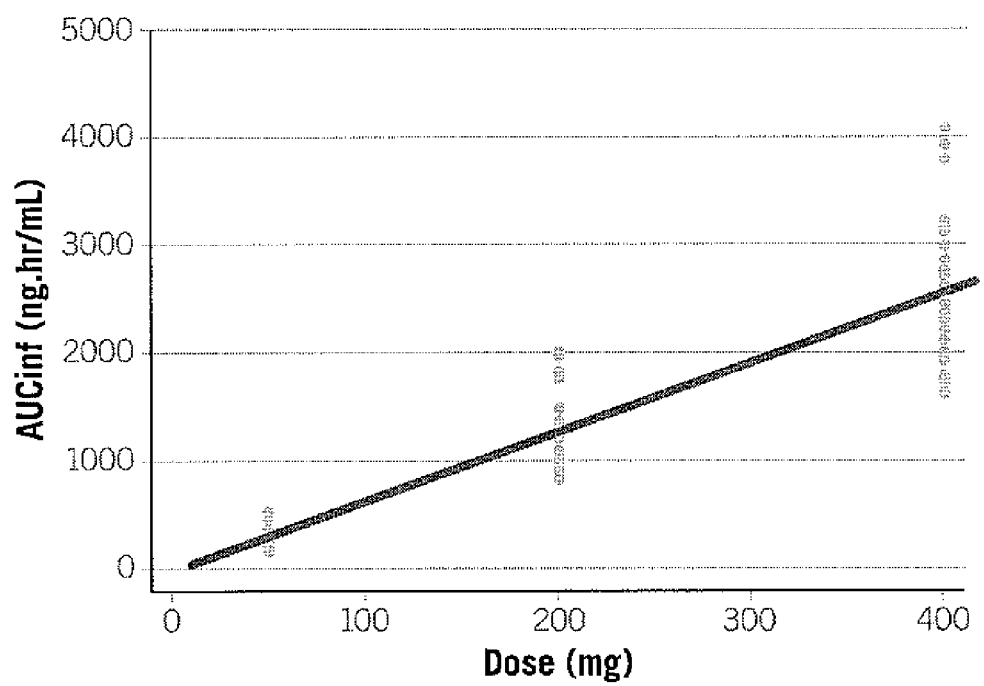
Figure 12:
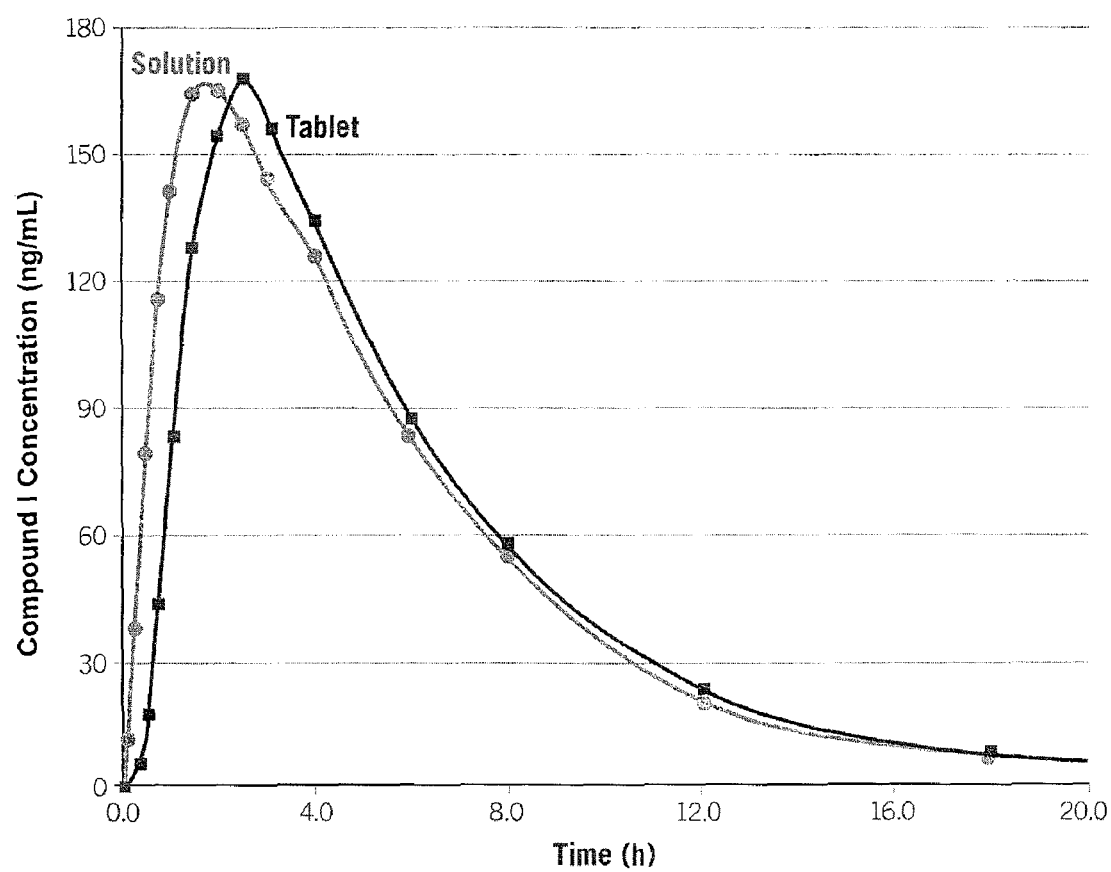
FIG. 12 is a graph that shows plasma-concentration time profiles for the 200 mg dose of Compound I given as an oral solution and as a tablet.
Figure 13:
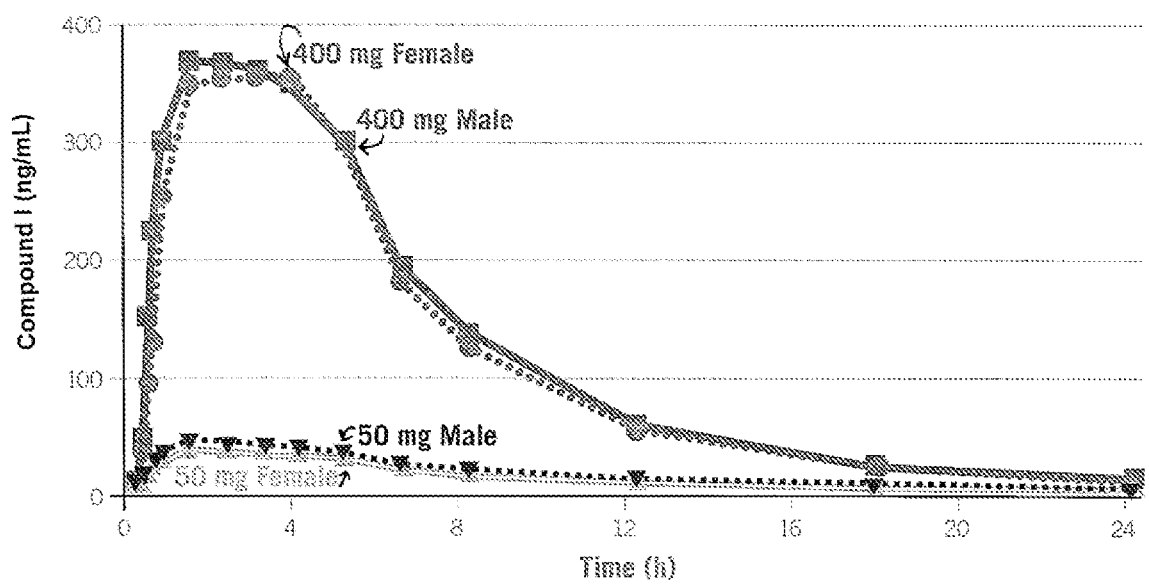
FIG. 13 is a graph that shows the mean Compound I plasma concentration profile following oral administration of 50 mg and 400 mg tablets, male and female.

Doses of 50 mg and above of both the solution and the tablet formulation achieved plasma levels previously associated with efficacy by the i.v. routes. The plasma-concentration time profile of Compound I following oral administration of solution doses of 50-400 mg compared to a 30 mg i.v. infusion is shown in FIG. 10. The pharmacokinetics of orally administered Compound I showed dose linearity from 25 to 400 mg in both males and females (FIGS. 11A and 11B). The relative bioavailability of the tablet to the solution was 100% as assessed at the 200 mg dose, achieving the same $C_{max}$ and AUC as the solution with only a slight delay in tmax (FIG. 12). The pharmacokinetic parameters of Compound I were similar following oral administration of the tablet formulation in males and females (FIG. 13).

In summary, no significant difference in bioavailability of 200 mg Compound I was observed for the tablet and solution formulations. Median $t_{max}$ after administration of 50 to 400 mg Compound I tablet formulation ranged between 1.5 and 2.5 hours. Dose proportionality of Compound I for $AUC_t$, $AUC_\infty$, and $C_{max}$ was observed in male and female subjects after administration of 50, 200, and 400 mg Compound I tablet formulation. Systemic exposure ($AUC_t$, $AUC_\infty$, and $C_{max}$) to Compound I was very similar in females compared to males after administration of 50 and 400 mg Compound I tablet formulation. The differences noted in $AUC_t$, $AUC_\infty$, and $C_{max}$ were of no clinical relevance.

Results: Safety

All doses of the solution and tablet formulations were well tolerated with no clinically significant effects on vital signs, ECGs or safety labs. Drowsiness, dizziness and paresthesia were the most common adverse events with both formulations—most reports were mild and none were severe. Interesting, parasthesiae, which were the most common drug-related adverse events after intravenous administration of Compound I, were substantially less common after oral administration. Adverse events were similar in both genders except that fatigue was more common in females (50%) than males (21%) after the 400 mg dose. A listing of treatment-emergent adverse events from Study 2 is shown in the Table 5 below:

TABLE 5

Adverse events related to Compound I (Study 2)

| Preferred term | Part 1 | | Part 2 | |
|---|---|---|---|---|
| | 200 mg tablet (N = 28) n (%) | 200 mg tablet (N = 29) n (%) | 50 mg tablet (N = 28) n (%) | 400 mg tablet (N = 28) n (%) |
| Overall | 12 (42.9) | 9 (31.0) | 8 (28.6) | 18 (64.3) |
| Palpitations | 0 | 0 | 1 (3.6) | 0 |
| Blurred vision | 0 | 0 | 0 | 1 (3.6) |
| Diarrhea | 1 (3.4) | 0 | 0 | 0 |
| Nausea | 1 (3.4) | 2 (7.1) | 3 (10.7) | 0 |
| Fatigue | 2 (6.9) | 1 (3.6) | 8 (28.6) | 9 (32.1) |
| Feeling hot | 0 | 0 | 0 | 1 (3.6) |
| Dizziness | 4 (13.8) | 5 (17.9) | 2 (7.1) | 5 (17.9) |
| Headache | 1 (3.4) | 0 | 0 | 1 (3.6) |
| Paresthesia | 3 (10.3) | 2 (7.1) | 2 (7.1) | 2 (7.1) |
| Somnolence | 3 (10.3) | 2 (7.1) | 2 (7.1) | 3 (10.7) |

N = number of subjects per treatment, n = number of subjects with treatment-emergent adverse events In conclusion, Compound I is orally bioavailable, and at doses of 50 mg and above achieves plasma levels previously associated with acute migraine efficacy after intravenous administration. The tablet formulation gives similar plasma profiles to an oral solution with the expected slight delay in $t_{max}$ associated with disintegration and dissolution of the tablet. By the oral route, Compound I shows dose proportionality with similar pharmacokinetics in males and females.

Example 5: Prediction of Therapeutically Effective Dose of Compound I Based on Relationship Between Plasma Concentrations and Headache Response The objective is to predict an oral dose range of Compound I that is at least as effective as sumatriptan in the acute treatment of migraine.

As background, Compound I, a neutrally acting antimigraine agent, is a selective agonist at 5-$HT_{1F}$ receptors that, unlike triptans, is not a vasoconstrictor. In a Phase II trial with an adaptive dose allocation design, the efficacy of Compound I given as an i.v. infusion was established (FIG. 6A). The relationship between plasma concentrations and headache response was analyzed using population pharmacokinetics-pharmacodynamic (PK-PD) modeling. A subsequent Phase I trial studied the PK of an oral liquid formulation of Compound I. Using the relationship between plasma levels and headache response, together with oral PK of Compound I, an oral dose range was predicted that is expected to provide acute migraine relief.

Methods

Phase II trial (intravenous infusion of Compound I over 20 min):

Doses: placebo (n=42), 2.5 mg (n=4), 5 mg (n=12), 10 mg (n=24), 20 mg (n=28), 30 mg (n=16), 45 mg (n=4). PK measured and headache scored (4 point scale; 0-3 no headache to severe headache) for 4 hours.

Phase I trial (oral liquid formulation of Compound):

Doses: 25 mg (n=6), 50 mg (n=6), 100 mg (n=14), 200 mg (n=6), 300 mg (n=6), and 400 mg (n=14). PK measured for 30 hours.

Background PK-PD Modeling

Figure 14:
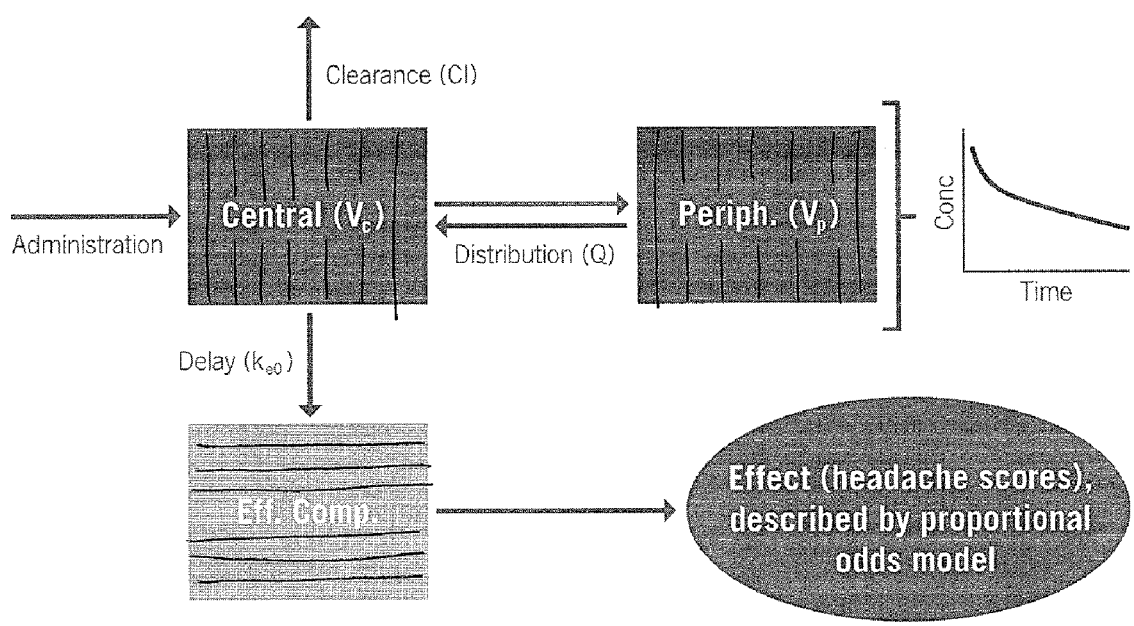
FIG. 14 is a schematic representation of PK-PD model. PK part is Central (Vc) and Periph. (Vp) (rectangles with vertical lines); hysteresis (delay) is Eff. Comp. (rectangle with horizontal lines); and PD part is Effect (headache scores) described by proportional odds model (oval).

Plasma concentration verses time profiles are described by compartmental models (FIG. 16, upper part): drug is assumed to distribute into one or more interconnected hypothetical compartments, which mimics drug absorption, distribution, and elimination processes. FIG. 14 is a schematic representation of a PK-PD model. PK part is indicated with rectangles having vertical lines, hysteresis (delay) is indicated with a rectangle having horizontal lines, and PD part is indicated with an oval.

Target site is often in an organ or peripheral tissue, rather than in plasma. Therefore, distribution to target site may cause delay (hysteresis). In general, this is accounted for using an "effect compartment model":

$$\frac{dC_e}{dt} = k_{e0} \times (C_p - C_e)$$

$C_e$: concentration at effect site; $C_p$: plasma concentration; $K_{eO}$: rate constant to describe delay The resulting continuous description of the concentration at the target site is linked to the observed effect using a PD model. Many PD models have been developed with varying complexity based on physiological and mechanistic assumptions.

Modeling Steps

1. A population PK-PD model was developed to describe the relationship between plasma concentration and headache response. Headache response was a categorical response (scores 0/1/2/3 i.e., none/mild/moderate/severe), which was modeled using a proportional odds model: "Estimation of time course probability to have a given score after administration of placebo (natural time course of attack) or drug (drug effect on headache)."

Example

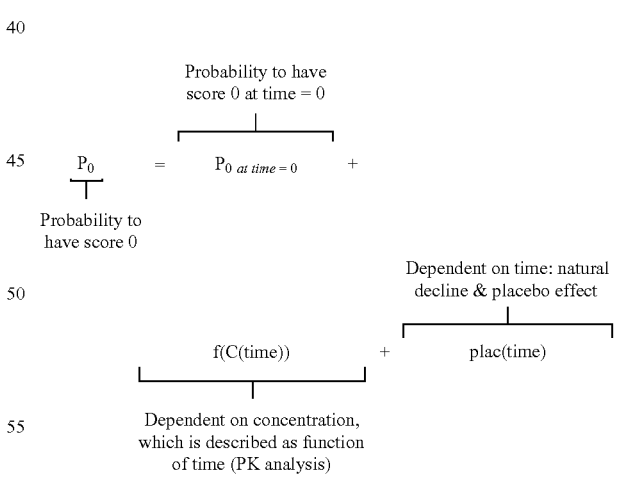

Hysteresis (delay) between plasma concentration and effect on headache response is described using "effect compartment model".

2. A population PK model was developed to describe the concentration-time profile of Compound I in plasma after oral administration.

3. Using the PK model for oral Compound I, combined with the concentration-effect relationship, the minimal effective oral dose of Compound I was predicted as follows:

Dose should give faster onset of headache response and/or higher response rate than intranasal sumatriptan (20 mg).

Pain Relief (score 3/2 to 1/0; placebo corrected) should be at least 12% after 30 min.

Placebo corrected Pain Relief was used, because headache response in placebo treated subjects differs between trials.

Data analysis was performed using NONMEM® version 6.2.

Figure 15:
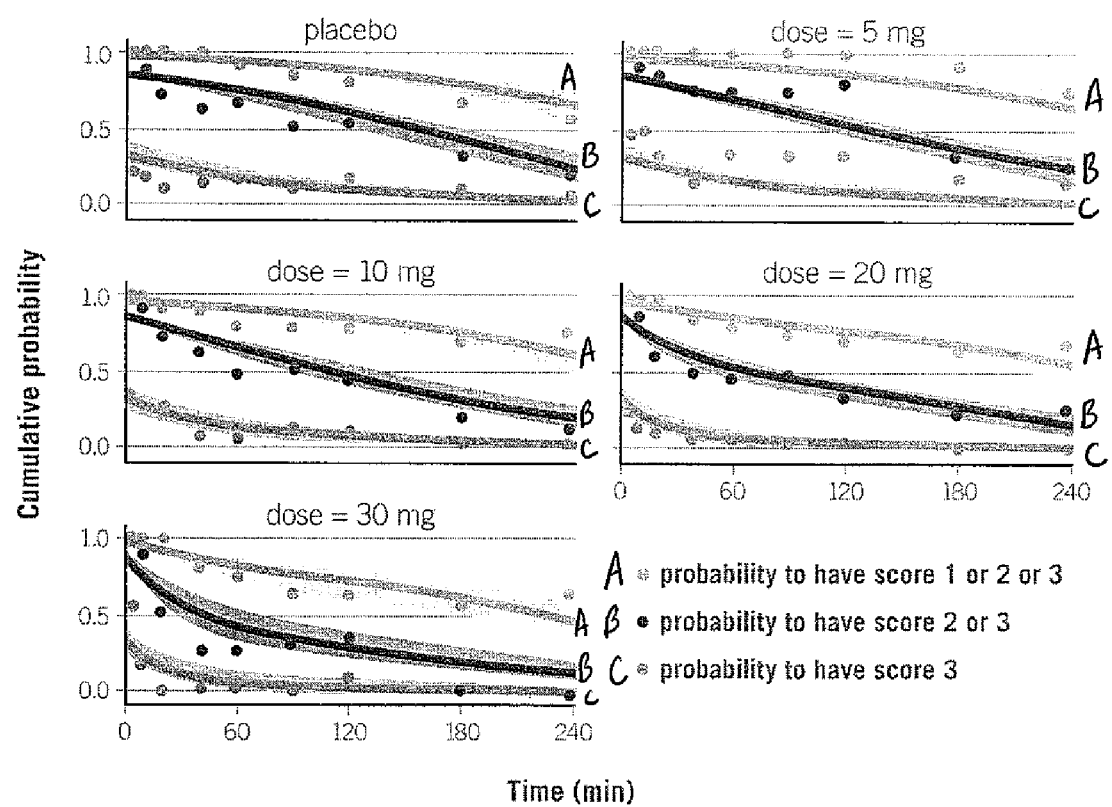
FIG. 15 is a series of graphs that show cumulative probability to have a certain headache score versus time following administration of Compound I. Dots represent observed headache response; lines represent predictions by PK-PD model; shaded areas indicate prediction uncertainty, obtained from the uncertainty of the parameter estimates. Doses were administered intravenously.
Figure 16:
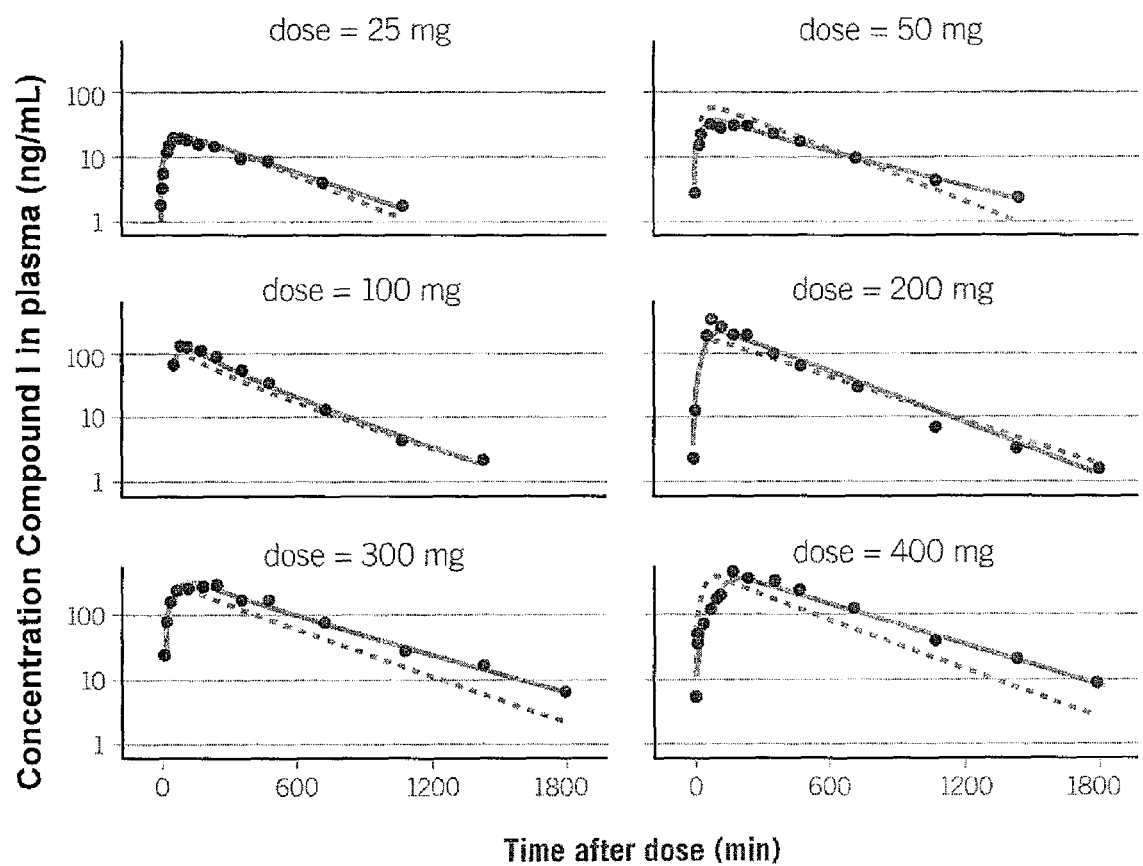
FIG. 16 is a series of graphs that show examples of concentration time profiles after different oral doses of Compound I. Dots represent plasma concentrations; lines represent individual predictions by PK model; broken lines represent population predictions by PK model (prediction for typical subject in population). Doses were administered orally.

Results:

The resulting PK-PD model adequately described the headache scores after all intravenous doses of Compound I (FIG. 15). FIG. 15 shows the cumulative probability to have a certain headache score versus time. Dots represent observed headache response; lines represent predictions by PK-PD model; shaded areas indicate prediction uncertainty, obtained from the uncertainty of the parameter estimates. Doses were administered intravenously. FIG. 16 shows examples of concentration time profiles after different oral doses. Dots represent measured plasma concentrations; lines represent individual represent individual predictions by PK model; broken lines represent population predictions by PK model (prediction for typical subject in population). Doses were administered orally.

Figure 17:
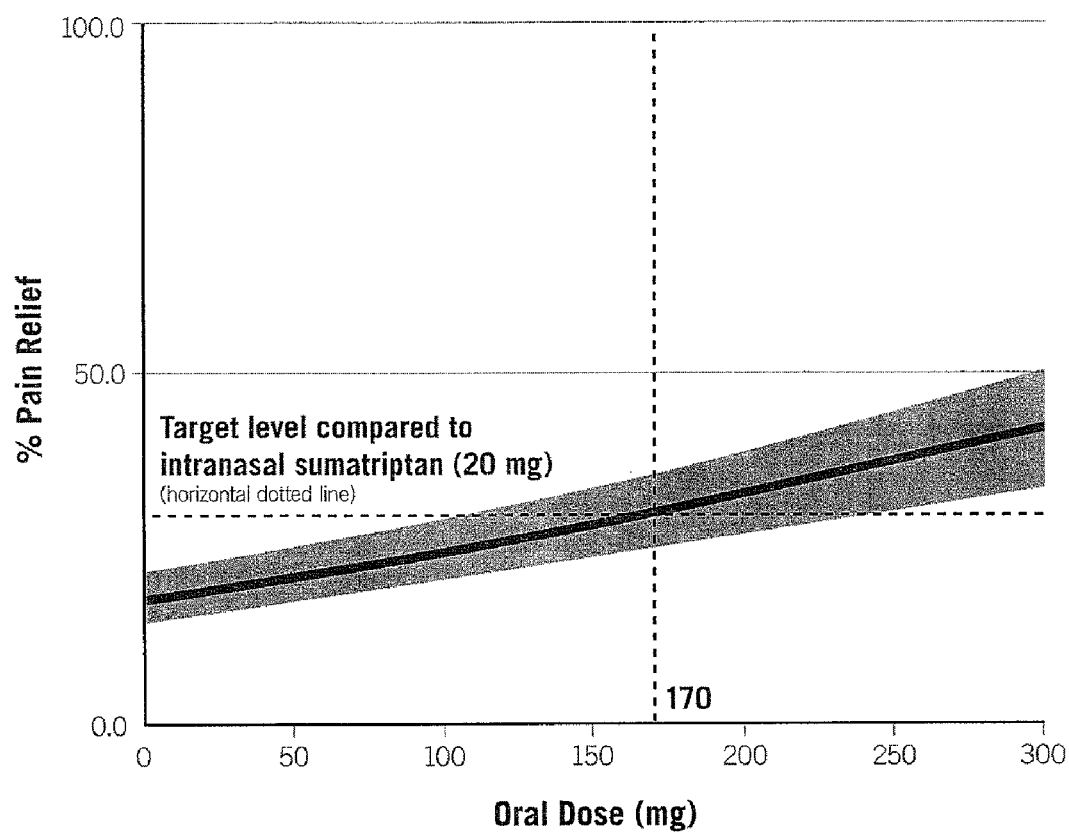
FIG. 17 is a graph that shows the percent pain relief at 30 minutes post dose of Compound I versus time to select an effective oral dose. Line represents median prediction of percent pain relief by PK-PD model; shaded areas indicate prediction uncertainty, obtained from the uncertainty of the parameter estimates. Target level compared to sumatriptan: placebo corrected pain relief should be at least 12%.

FIG. 17 shows the percent pain relief at 30 minutes post dose versus time to select an effective dose. Line represents median prediction of percent pain relief by PK-PD model; shaded areas indicate prediction uncertainty, obtained from the uncertainty of the parameter estimates. Target level compared to intranasal sumatriptan; placebo corrected pain relief should be at least 12%. Since the placebo response in the Phase II trial was 18%; pain relief is at least 30%.

The PK model adequately described the concentration-time profiles after oral administration of different doses of Compound I (FIG. 16). The model was used to predict migraine relief at 30 minutes after oral dosing of Compound I (FIG. 17). The target level derived from published sumatriptan data is indicated in FIG. 17. The predicted oral dose range needed to reach the desired therapeutic target is 170 mg and above.

Thus, a PK-PD model was developed, which adequately described the relation between plasma concentration and response (headache scores). On the basis of this concentration versus response relationship, an effective dose range 50-400 mg for an oral dose ranging study in migraine using an oral tablet formulation was identified.

INCORPORATION BY REFERENCE

The entire disclosure of each of the patent documents, including certificates of correction, patent application documents, scientific articles, governmental reports, websites, and other references referred to herein is incorporated by reference in its entirety for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed:

1. A method for the acute treatment of migraine in a human subject in need thereof consisting of oral administration to said subject a pharmaceutical composition adapted for oral delivery, the composition comprising 50 to 200 mg of 2,4,6-trifluoro-N-[6-(1-methyl-piperidin-4-ylcarbonyl)-pyridin-2-yl]-benzamide, or a pharmaceutically acceptable salt thereof, and a pharmaceutically acceptable diluent or carrier, wherein said composition is administered up to 200 mg daily.

2. The method of claim 1, consisting of oral administration to a subject in need thereof of 50 mg, 100 mg, or 200 mg of 2,4,6-trifluoro-N-[6-(1-methyl-piperidin-4-ylcarbonyl)-pyridin-2-yl]-benzamide hemisuccinate one time daily.

3. The method of claim 2, consisting of oral administration to a subject in need thereof, of 50 mg of 2,4,6-trifluoro-N-[6-(1-methyl-piperidin-4-ylcarbonyl)-pyridin-2-yl]-benzamide hemisuccinate salt one time daily.

4. The method of claim 2, consisting of oral administration to a subject in need thereof, of 100 mg of 2,4,6-trifluoro-N-[6-(1-methyl-piperidin-4-ylcarbonyl)-pyridin-2-yl]-benzamide hemisuccinate salt one time daily.

5. The method of claim 2, consisting of oral administration to a subject in need thereof, of 200 mg of 2,4,6-trifluoro-N-[6-(1-methyl-piperidin-4-ylcarbonyl)-pyridin-2-yl]-benzamide hemisuccinate salt one time daily.

* * * * *

UNITED STATES PATENT AND TRADEMARK OFFICE
CERTIFICATE OF CORRECTION

PATENT NO. : 12,257,246 B2  
APPLICATION NO. : 17/474203  
DATED : March 25, 2025  
INVENTOR(S) : Alison Pilgrim, James F. White and Nadia M. J. Rupniak Page 1 of 1

It is certified that error appears in the above-identified patent and that said Letters Patent is hereby corrected as shown below:

On the Title Page

Column 1, item (54) Invention Title and in the Specification Column 1, Lines 1-4: Delete the "[" preceding "-BEZAMIDE" and insert -- ] --, therefor.

Signed and Sealed this  
Nineteenth Day of August, 2025

Coke Morgan Stewart  
*Acting Director of the United States Patent and Trademark Office*